US 6,579,693 B1

(12) United States Patent
Bellamine et al.

(10) Patent No.: US 6,579,693 B1
(45) Date of Patent: Jun. 17, 2003

(54) GENETICALLY ENGINEERED YEAST STRAINS

(75) Inventors: Aouatef Bellamine, Paris (FR); Frédéric Delorme, Palaiseau (FR); Alain Perret, Villepreux (FR); Denis Pompon, Gif-sur-Yvette (FR)

(73) Assignees: Aventis Pharma S.A., Antony (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/495,901

(22) Filed: Feb. 2, 2000

Related U.S. Application Data

(62) Division of application No. 09/043,239, filed as application No. PCT/FR96/01413 on May 4, 1998, now Pat. No. 6,117,649.

(30) Foreign Application Priority Data

Sep. 15, 1995 (FR) .............................................. 95 10826

(51) Int. Cl.[7] .............................. C12Q 1/02; C12Q 1/26
(52) U.S. Cl. ................................ 435/29; 435/6; 435/25; 435/58; 435/69.1
(58) Field of Search .......................... 435/6, 29, 69.1, 435/254.11, 254.21, 58

(56) References Cited

U.S. PATENT DOCUMENTS 5,635,369 A * 6/1997 Pompon et al.

OTHER PUBLICATIONS

Eugster et al., *Saccharomyces cerevisiae*: An alternative source for human microsomal liver enzymes and its use in drug interaction studies, Toxicology, vol. 82, pp. 61–73 (1990).

Guengerich et al., Oxidation of Dihydropyridine Calcium Channel Blockers and Analogs by Human Liver Cytochrome P–450 IIIA4, J. Med. Chem. 34: 1838–1844 (1991). (Abstract).

Miyata et al., Isolation and Characterization of Human Liver Cytochrome b5 cDNA, Pharmacological Research 21(5): 513–520 (1989). (Abstract).

Peyronneau et al., Optimization of yeast–expressed human liver cytochrome P450 3A4 catalytic activities by coexpressing NADPH–cytochrome P450 reductase and cytochrome b5, Eur. J. Biochem 207: 109–116 (1992).

Renaud et al., Expression of human liver cytochrome P450 IIIA4 in yeast. A functional model for the hepatic enzyme, Eur. J. Biochem., 194: 889–896 (1990). (Abstract).

Truan et al., Enhanced in vivo moonoxygenase activities of mamalian P450s in engineered yeast cells producing high levels of NADPH–P450 reductase and human cytochrome b5, Gene 125: 49–55 (1993).

Urban et al., Maximizing the expression of mamalian cytochrome P–450 monooxygenase activities in yeast cells, Biochimie, vol. 72, pp. 463–472 (1990).

Urban et al., Xenobiotic metabolism in humanized yeast; engineered yeast cells producing human NADPH–cytochrome P–450 reductase, cytochrome b5, epoxide hydrolase and P–450s, Biochemical Society Transactions 21: 1028–1034 (1993). (Abstract).

Yamano et al., Human NADPH–P450 Oxidoreductase: Complementary DNA Cloning, Sequence and Vaccinia Virus–Mediated Expression and Localization of the CYPOR Gene to Chromosome 7, Molecular Pharmacology 35: 83–88 (1989). (Abstract).

* cited by examiner

*Primary Examiner*—Remy Yucel
*Assistant Examiner*—Bronwen M. Loeb
(74) *Attorney, Agent, or Firm*—Finnegan, Henderson, Farabow, Garrett & Dunner LLP

(57) ABSTRACT

Yeast strains expressing human genes coding regulating cytochrome P450 expression, a method for making same and applications thereof are described.

40 Claims, 20 Drawing Sheets

GENETICALLY ENGINEERED YEAST STRAINS

Figure 1:
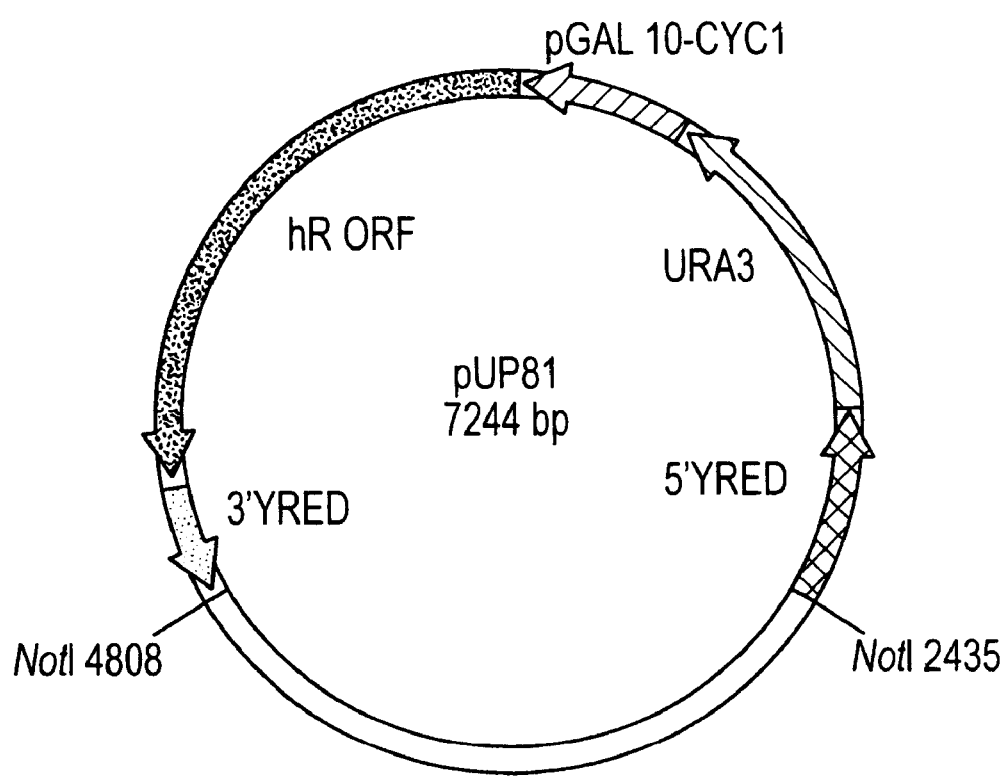

This is a continuation of application Ser. No. 09/043,239, filed May 4, 1998, now U.S. Pat. No. 6,112,649, which is the national stage of international application No. PCT/FR96/01413, filed Sep. 13, 1996, which are incorporated by reference herein.

The present invention relates to novel yeast strains which express cytochrome P450 activity, and to their use. It relates, in particular, to yeast strains which are able to produce a system of human cytochrome P450 enzymes, and to the plasmids which are used for constructing these strains.

The P450 cytochromes constitute a superfamily of membrane enzymes. These enzymes are monooxygenases which are involved, more specifically, in the metabolism of xenobiotics and drugs.

They are used, in particular, for:

diagnosing in vitro the formation of toxic or mutagenic metabolites by the human hepatic metabolism of natural or artificial xenobiotic molecules (pollutants, drugs or additives). This diagnosis is of prime importance for developing new pharmaceutical molecules, identifying and destroying toxic or pollutant molecules from the environment, and producing metabolites.

Because of their involvement; at one and the same time, in these detoxification processes and these toxicity phenomena, these proteins have been studied intensively (Guenguerich, 1988).

Nevertheless, these studies have rapidly come up against difficulties such as that of studying individual forms of P450 cytochromes. Heterologous expression systems have therefore been developed to overcome these problems.

The use of mammalian cells as hosts for heterologous expression has been developed since 1986 (Zuber et al., 1986). While these systems have the advantage of being closely related to hepatic cells (main location of the P450 cytochromes), they unfortunately suffer from low levels of expression.

While prokaryotic hosts, such as bacteria, admittedly enable substantial quantities of correctly folded cytochrome P450 to be obtained (Barnes et al., 1991), modifications of the 5'-terminal expressed part of the DNA, which cannot be circumvented, are observed with this type of host (Doehmer & Greim, 1992).

On the other hand, it is very particularly advantageous to choose eukaryotic hosts of the yeast type: this organism makes it possible to achieve conditions which are similar to those of human hepatic cells and gives rise to a high level of protein expression. Furthermore, yeast possesses, in endogenous form, all the enzymic machinery which is required for expressing membrane proteins of the cytochrome P450 type and their associated enzymes; thus, yeast has available a cytochrome b5 and an NADPH-cytochrome P450 reductase, i.e. two enzymes whose presence is required for cytochrome P450 to function.

Yeast therefore offers an advantageous solution to the different problems (Oeda K. et al., 1985; Pompon, 1988), since, with this organism:

the N-terminal sequences of the proteins which are expressed do not have to be modified (as is the case with expression in bacteria)

reasonable quantities of heterologous cytochrome P450 are obtained for various biochemical and structural studies, a system of associated enzymes already exists in the organism.

Yeasts which have been specially studied for expressing heterologous proteins and which may in particular be mentioned are Kluyveromyces, Pichia, Hansenula, Candida and Saccharomyces, whose genome structures are well known. Various systems for expressing cytochrome P450 in yeasts have been described in the literature.

In strains termed first generation strains, P450 cytochromes have been expressed from plasmids and use the NADPH-cytochrome P450 reductase and the cytochrome b5 which are endogenous to yeast as electron donors (Pompon, 1988; Cullin & Pompon, 1988).

A first improvement of this system gave rise to strains termed second generation strains in which, yeast cytochrome P450 reductase was overexpressed (under the control of the GAL10-CYC1 promoter) and a human cytochrome b5 was coexpressed (patent WO93/02200 and Truan et al., 1993). These strains thus made it possible to obtain recombinant cytochrome P450 enzymic activities which were from 5 to 60 times greater in the isoform than in the starting strain.

Nevertheless, the existing systems are not entirely satisfactory: either they do not enable adequate expression of the proteins to be obtained, or the proteins which are obtained are not sufficiently similar to the human system.

The specific objective of the present invention is to propose a third strain generation which does not suffer from the abovementioned drawbacks. Unexpectedly, the Applicant demonstrated that it was possible simultaneously to replace both the yeast NADPH-cytochrome P450 reductase and the yeast cytochrome b5 with their human homologues. This is all the more surprising since simultaneous disruption of these two genes was known to be lethal in yeast and, until now, it has not been possible to obtain a viable strain in which these two genes are deleted.

In the strains which are claimed, the yeast cytochrome P450 reductase and/or the yeast cytochrome b5 have been replaced with their human homologue(s). This, very advantageously, makes it possible to create a system which is very similar to hepatic cells, given the fact that the whole multienzyme system is then of the same nature.

This novel system makes it possible to study the effect of the nature of the redox partners of the P450 cytochromes which are expressed as well as the stoichiometries which are required to obtain cytochrome P450 activities which are comparable to those which exist in liver.

The invention therefore relates, initially, to a genetically modified yeast strain which is characterized in that:

Firstly, the genes encoding the endogenous cytochrome b5 and the endogenous NADPH-cytochrome P450 reductase have been inactivated, Secondly, it comprises a nucleic acid which encodes human NADPH-cytochrome P450 reductase, Thirdly, it comprises a nucleic acid which encodes human cytochrome b5.

The nucleic acids which are used for integrating genes encoding human cytochrome b5 and human reductase into the strain are preferably cDNAs. The cDNAs containing the totality of the sequences encoding these two proteins have been isolated and sequenced (in the case of human reductase, see S. Yamano et al. Mol. Pharmacol. 1989 Vol. 36: 83–8, and, in the case of human cytochrome b5, see M. Miyata et al. Pharmacol. Res. 1989 Vol. 21: 513–20).

Very preferably, also, the selected yeast is *Saccharomyces cerevisiae*.

Within the meaning of the present invention, an inactivated gene is understood as being a gene which has been rendered incapable of encoding its natural protein. The inability of the said genes to encode their natural proteins can be manifested either by the production of a protein which is inactive due to structural or conformational alterations, or by the absence of production, or by production of the natural protein at an attenuated level.

Various methods can be used to inactivate the native genes:

- total or partial deletion of the gene. Deletion is understood as being any removal of the gene under consideration. This removal can be of a part of the region encoding the protein and/or of all or part of the transcription promoter region,
- one or more point mutations in the gene. The mutations can be obtained by treatment with chemical mutagenic agents (such as alkylating, bialkylating or intercalating agents) or with physical mutagenic agents (X, gamma or ultraviolet rays), or by means of site-directed mutagenesis,
- a mutational insertion due to the action of restriction enzymes, which interrupt the reading frame of the gene and inactivate the latter, and/or,
- a gene disruption, for example in accordance with the protocol initially described by Rothstein [Meth. Enzymol. (1983)202]. In this case, the integrity of the coding sequence, will be disrupted in order to enable the wild-type sequence to be replaced, by means of homologous recombination, with a sequence which encodes the corresponding human protein.

According to the present invention, preference is given to using the method of gene disruption, as described below.

Various solutions are conceivable for transforming the claimed strains with a view to causing them to express the human enzymes according to the invention; on the one hand, it is possible to transform a wild-type strain, one of whose genes has been inactivated, with a replicative plasmid which contains the nucleic acid encoding the corresponding human protein. In this case, the nucleic acid is not integrated into the genome of the yeast.

On the other hand, it is possible to integrate a nucleic acid, in the form of a cDNA which encompasses the sequence encoding the human protein in question, into the genome of the yeast. In this case, the integration can be effected either into a known locus on this genome corresponding to a marker gene, thereby altering neither the reproductive properties of the yeast nor its viability, or at the site occupied by the inactivated native gene.

Both the nucleic acid encoding the reductase and the nucleic acid encoding the cytochrome b5 can be introduced into the strain using one of these methods.

According to the present invention, and in order to improve the stability of the strain and to achieve more favourable conditions, preference is given to choosing the embodiment which consists in integrating the nucleic acid encoding human NADPH-cytochrome P450 reductase and/ or the nucleic acid encoding human-cytochrome b5 into the genome of the yeast, with a preferred embodiment of the present invention being to integrate these nucleic acids into the site of, and in place of, the endogenous genes.

According to another preferred embodiment of the present invention, the gene encoding human cytochrome b5 is integrated into an intergenic site for a marker gene, in particular into the SPL1/leu2 intergenic site.

The invention also relates to a strain which is characterized in that the nucleic acid encoding human cytochrome b5 is integrated into the genome.

A particular embodiment of the invention consists in introducing two cytochrome b5 copies into the transformed strain.

Another problem encountered by the Applicant is that of expressing human genes in yeast at an adequate level.

For this, it is advantageous for these genes to be placed under the control of a yeast promoter which enables them to be expressed. These yeast promoters can either be inducible or be constitutive. In the present application, a constitutive promoter is understood as being a promoter whose expression is constant under the standard culturing conditions. According to the present invention, at least one of the human genes is under the control of a constitutive yeast promoter.

This promoter is selected from the known promoters. The promoters of the genes for isocytochrome C1 (CYC1), alcohol dehydrogenase (ADH1), transcription elongation factor (TEF), yeast glyceraldehyde phosphodehydrogenase (GAPDH below) and yeast phosphoglycerate kinase (PGK below) can, for example, be used.

The promoter is preferably selected from the promoter of the gene for yeast glyceraldehyde phosphodehydrogenase, the promoter of the gene for yeast phosphoglycerate kinase and the endogenous promoter of yeast cytochrome b5. It should be pointed out that, in a particular embodiment of the invention, the gene encoding human cytochrome b5 is under the control of the endogenous Yb5 promoter.

The inducible promoter is preferably selected from the GAL10 and CYC1-GAL10 promoters.

It was previously not possible to obtain haploid strains which exhibited the characteristics which are of interest to us, that is inactivation of the abovementioned endogenous genes and replacement of these genes with nucleic acids encoding the corresponding human genes. There was no alternative but to use the diploid form. One of the advantages of the present invention is that of being able to work with haploid yeasts, thereby making it possible to achieve a greater degree of stability and to avoid unwanted recombinations.

According to a preferred embodiment of the invention, the strains are therefore characterized in that they are haploid.

The strains according to the invention possess at least one nucleic acid encoding human cytochrome P450. The said nucleic acid will preferably be integrated on a plasmid. The customary techniques can be used to transform the humanized yeast strains according to the invention with a plasmid for expressing any cytochrome P450, provided that the selection markers of the said plasmid are compatible with the yeast strains which have been developed. In particular, such plasmids can be obtained by using the techniques of the art to clone the coding sequence of a cDNA encoding any human cytochrome P450 into the cloning polylinker of the plasmid pYeDP60 (see materials and methods).

The cytochrome P450 can be selected, in particular, from the human P450 cytochromes 1A1, 1A2, 1B1, 2C8, 2C9, 2C18, 2C19, 2E1, 3A4 and 3A5. The humanized strains according to the present application exhibit indisputable advantages for expression as compared with the wild-type yeasts and as compared with the previously developed recombinant strains.

The invention also relates to a yeast strain according to the invention which is additionally caused to express the monooxygenase activity of a human cytochrome P450 which is carried by a plasmid.

Another embodiment of the invention consists in causing the previously described additional copy of the nucleic acid encoding cytochrome b5 to be incorporated into a plasmid and, in particular, to be incorporated into the plasmid which already contains a copy of the nucleic acid encoding the cytochrome P450. This is because it is particularly advantageous, for obtaining optimum activity of the P450, to be able to achieve a relative molar stoichiometry of at least 1/1 in the levels at which the human cytochrome b5 and the human P450 are expressed. The genomic integration of a single copy of the cytochrome b5 gene can, under certain circumstances, prove to be inadequate from the viewpoint of the high level of expression of the P450, as results from its expression from a multicopy plasmid according to the invention. Thus, the present-invention makes it possible to improve still further the efficacy of the system by describing the construction of a series of plasmids which carry, at one and the same time, a cassette for expressing the cytochrome P450 of interest and a cassette for expressing cytochrome b5. The specific structure of these plasmids makes it possible to achieve stable expression which is at a high level and where there is adequate stoichiometry between the two cytochromes. These plasmids are compatible with all the strains described in the application. Their use can also be extended to other strains.

The preferred object of the present invention is to develop a yeast strain which exhibits all the previously described characteristics. Several intermediates which were constructed for the purpose of achieving this strain are described.

In the present invention, the starting strains are preferably those which are described in the literature, in particular:
- the strain W(ΔB), which is described by Truan et al., and in which the gene encoding the yeast cytochrome b5 (termed Yb5 below) has been disrupted. In order to achieve this, a vector is constructed which possesses the HIS3 marker gene integrated into a restriction site in the cytochrome b5 gene. This vector is used to transform a diploid HIS3⁻ strain. The recombinants are selected,
- the strain W(R), in which the gene encoding yeast reductase has not been inactivated,
- and the strain W(hR), which is obtained from a W(RΔ) strain by means of transformation with the vector pUP81 (FIG. 1). In this strain, the gene encoding the inactivated yeast reductase (termed YRED below) has been replaced by inserting a cassette which contains the inducible promoter and the sequence encoding human reductase (termed HRED below).

These strains are crossed and then sporulated, and the haploid W(hR,ΔB) strains are selected which are deleted for Yb5 and YRED and which express human reductase under the control of the GAL10-CYC1 promoter.

In this respect, the invention also relates to a strain which comprises a nucleic acid encoding human NADPH-cytochrome P450 reductase under the control of the GAL10-CYC1 promoter and whose genes encoding yeast cytochrome b5 and yeast NADPH-cytochrome P450 reductase have been inactivated (strain W(hR,ΔB)).

Another strain which is preferred according to the invention consists of a strain which is identical to the preceding strain but in which the inducible GAL10-CYC1 promoter has been replaced with the GAPDH promoter.

This replacement can be effected by transforming with the plasmid pAB2 (FIG. 4), which is constructed from pUP81 (FIG. 9) and which contains a cDNA encoding HRED under the control of the constitutive GAPDH promoter. The transformants are selected using the method described in patent WO94/01564. The strain which is obtained is designated W(GhR,ΔB). In this strain, the sequence encoding human reductase is under the control of the constitutive yeast GAPDH promoter, and the yeast cytochrome b5 and YRED are inactivated.

The invention also relates to a strain which is characterized in that the nucleic acid encoding human NADPH-cytochrome P450 reductase is under the control of the promoter of the gene for yeast glyceraldehydephosphodehydrogenase.

Another strain which is preferred according to the invention is obtained from the W(hR,ΔB) strain by means of transformation with the vector pAB3 (FIG. 6 and 12), which contains the sequence encoding human cytochrome b5. Yeasts are selected which have integrated this vector. The resulting strain is termed W(hR,hb5). This strain possesses the two sequences which encode human proteins.

In order to construct a strain which is particularly advantageous according to the invention, the strain W(GhR,ΔB) is transformed with the plasmid pAB3 in the same manner as before. This results in a strain, W(GhR,hb5), which possesses the properties of the two preceding strains, namely that it expresses the gene encoding human reductase under the control of the yeast GAPDH promoter and that it can also express the gene encoding human cytochrome b5 under the control of the yeast pYb5 promoter.

In a manner which is equally well preferred, the Applicant has constructed a strain from the W(hR,ΔB) strain. This strain is transformed with the plasmid vector pAP1 (FIG. 8 and 13), which has been previously linearized with a restriction enzyme. The transformants are selected which have integrated the sequence encoding human cytochrome b5 under the control of the yeast PGK (phosphoglycerate kinase) promoter, carried by pAP1 into the leu2/SPL1 intergenic site of the yeast chromosome (FIG. 14).

In the Applicant's nomenclature, this strain has the designation W(hR,Lhb5). It is able to express the sequence encoding human reductase under the control of the GAL10-CYC1 promoter and the sequence encoding cytochrome b5 under the control of the yeast PGK promoter.

The invention also relates to a yeast strain which is characterized in that it comprises at least one nucleic acid which encodes human cytochrome b5 under the control of the promoter of the gene for yeast phosphoglycerate kinase.

Very particular preference is given to the following strain. The starting strain is the strain W(GhR,ΔB), which is transformed with the linearized pAP1 vector. The clones are selected which have integrated the sequence encoding human cytochrome b5 under the control of the yeast PGK promoter into the abovementioned leu2/SPL1 chromosomal site.

This thereby results in a strain, W(GhR,Lhb5), which comprises the sequences encoding the two human genes under the control of two constitutive yeast promoters.

Another part of the subject-matter of the invention is characterized in that a strain comprises, at one and the same time:
- the nucleic acid encoding human NADPH-cytochrome P450-reductase under the control of the promoter of the gene for yeast glyceraldehyde phosphodehydrogenase,
- and the nucleic acid encoding human cytochrome b5 under the control of the promoter of the gene for yeast phosphoglycerate kinase.

Another embodiment of the invention consists in starting with the strain W(R) and transforming it with the pAP1 vector; after selection, the strain W(R,Lhb5,Yb5) is obtained.

Preference is given to starting with the strain W(hR), which is then transformed in the same manner; after selection, the strain W(hR,Lhb5,Yb5) is obtained.

The strains which have been constructed in accordance with the present invention make it possible to develop processes which are directed towards evaluating the toxicity of the metabolites which arise from the degradation of novel chemical molecules by the cytochrome P450 enzyme system.

The invention also relates to a process for evaluating the toxicity of a compound, characterized in that:
the said compound is brought into contact with a yeast according to the invention or with an enzyme preparation which is derived from such a yeast, and the toxicity of the metabolites which are produced is analysed.

The present invention furthermore makes it possible to obtain an enzyme complex which is very similar to that which exists in human hepatic cells. This provides the possibility of working in vitro under favourable conditions for expressing human enzymes. Thus, it is possible to determine the metabolites which will result, in man, from the degradation of novel chemical compounds by the cytochrome P450 complex.

The invention also relates to a method for determining in vitro the human metabolites of a chemical compound, characterized in that:
the said compound is brought into contact with a yeast according to the invention, or with an enzyme preparation which is derived from such a yeast, and the metabolites which are produced are identified.

The present invention is described in more detail with the aid of the examples which follow and which should be regarded as being illustrative and not limiting.

FIGURE DESCRIPTIONS

FIG. 1: plasmid pUP81.

Figure 2:
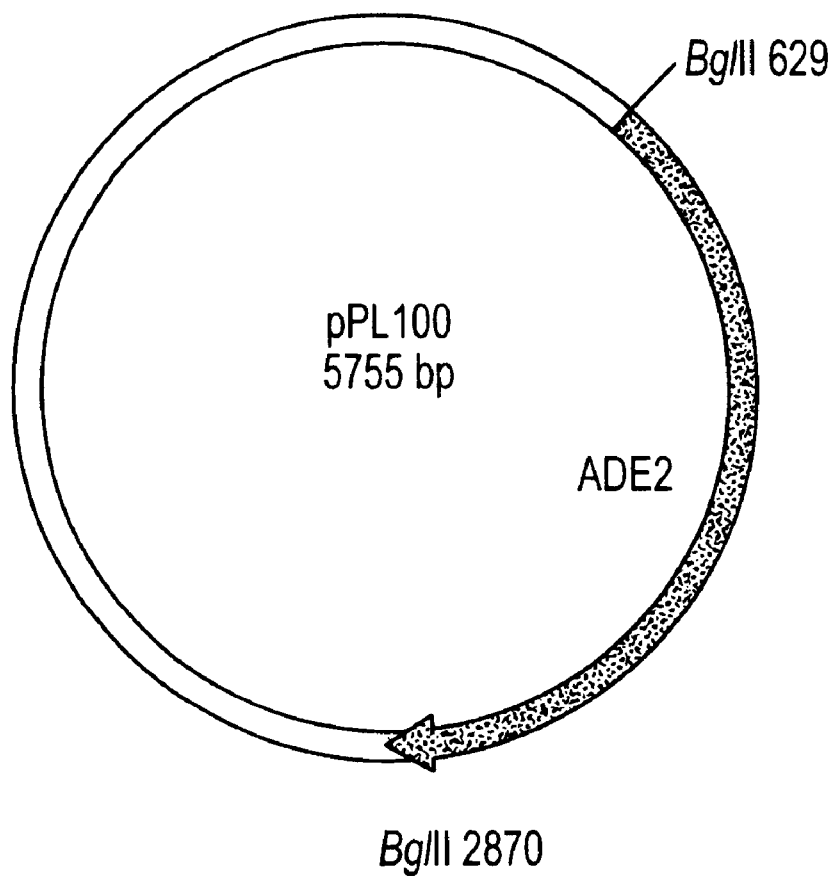

FIG. 2: plasmid PPL100.

Figure 3:
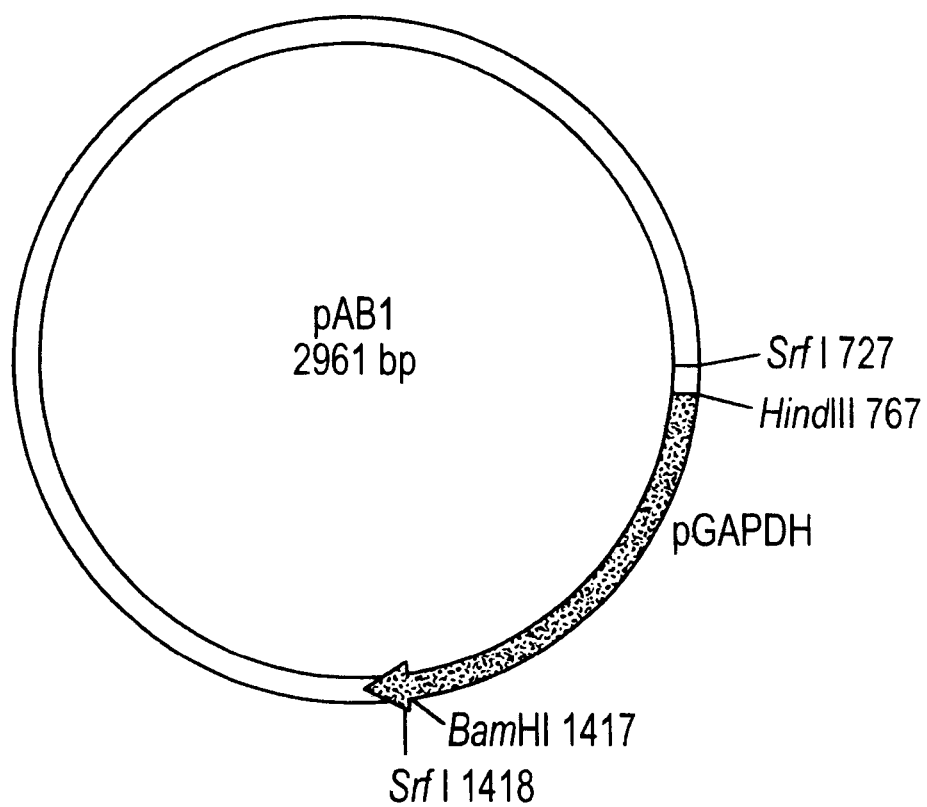

FIG. 3: plasmid pAB1.

Figure 4:
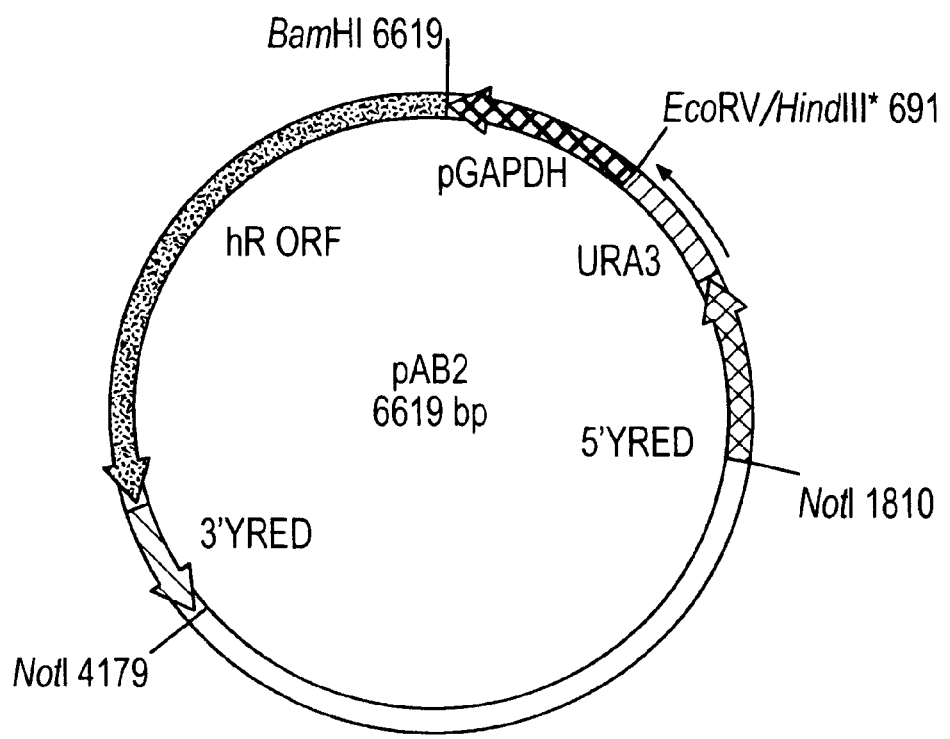

FIG. 4: plasmid pAB2.

Figure 5:
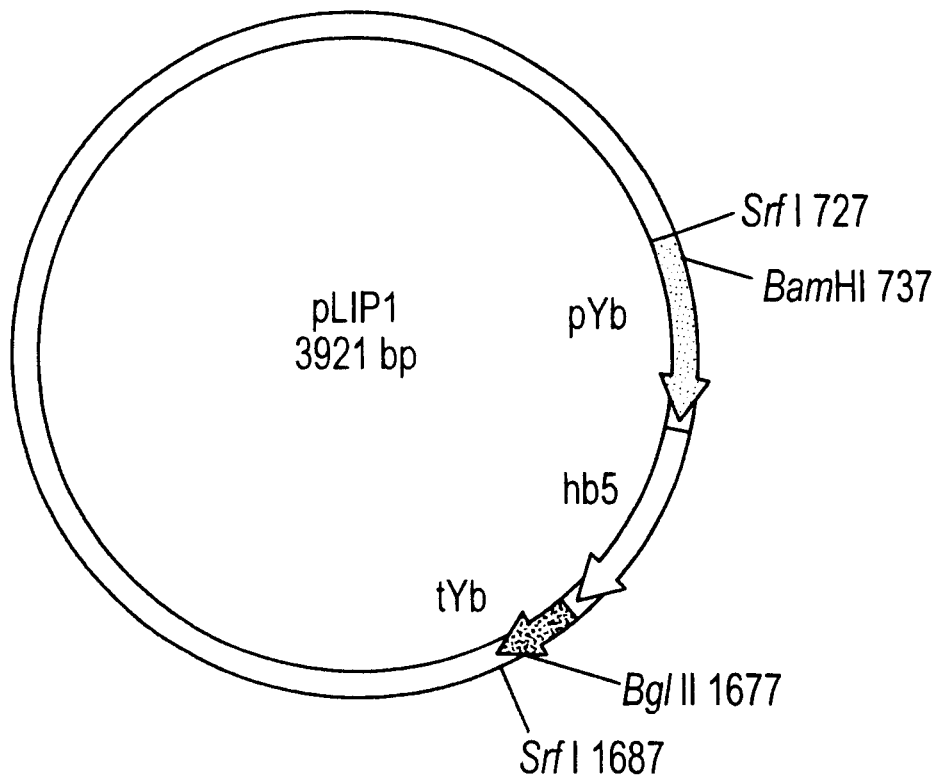

FIG. 5: plasmid pLIP1.

Figure 6:
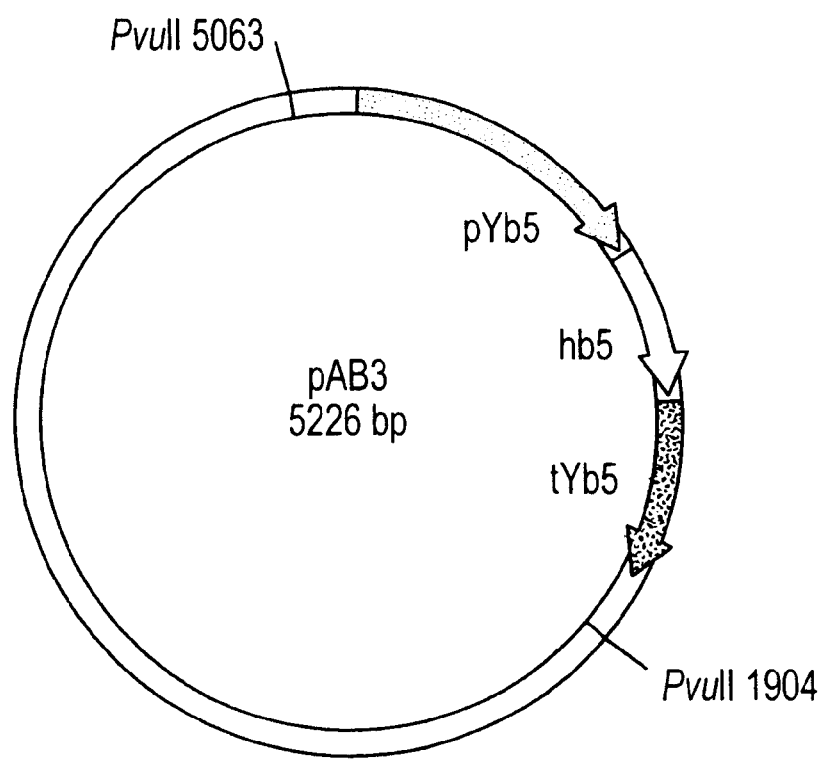

FIG. 6: plasmid pAB3.

Figure 7:
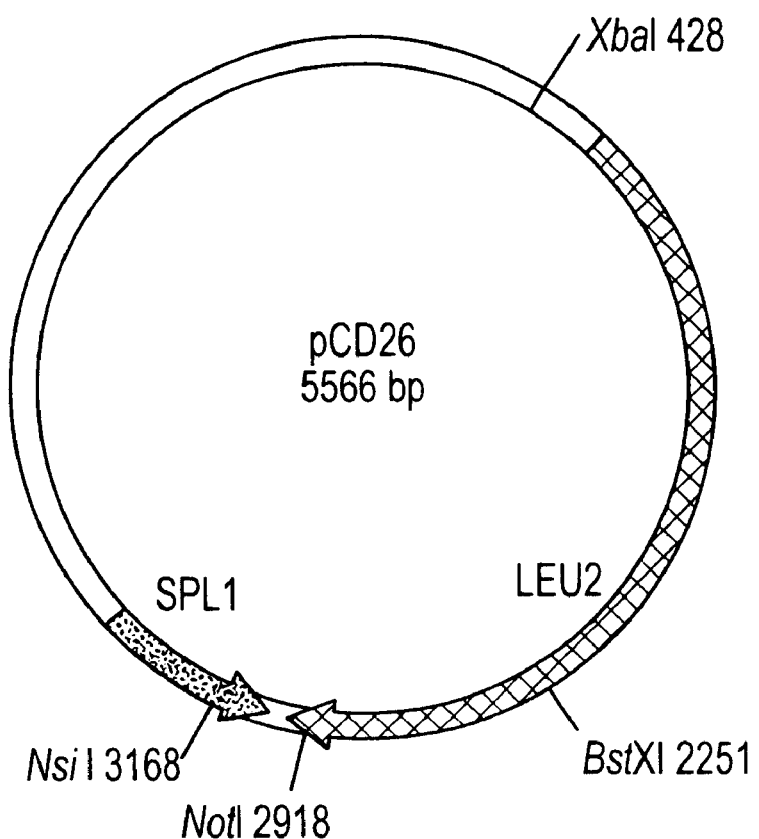

FIG. 7: plasmid pCD26.

Figure 8:
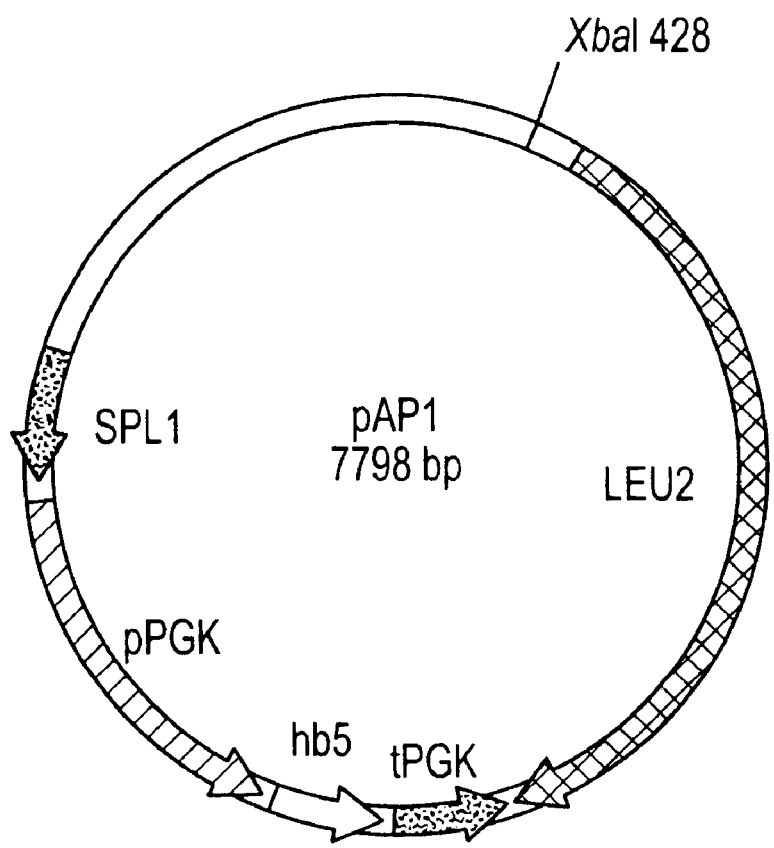

FIG. 8: plasmid pAP1.

Figure 9:
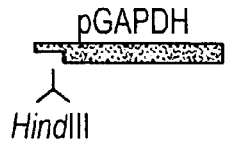
Figure 9:
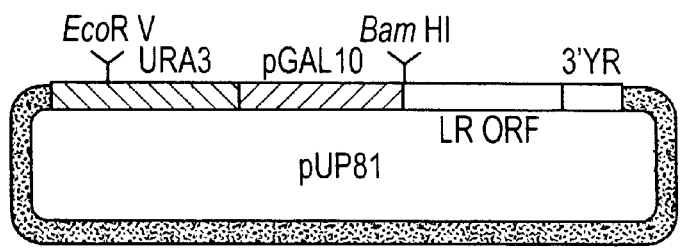
Figure 9:
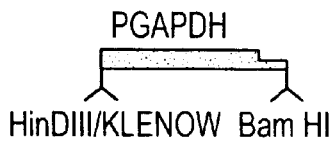
Figure 9:
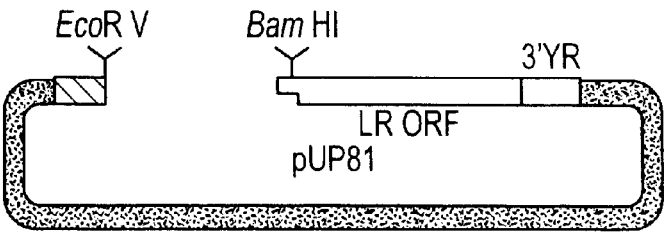
Figure 9:
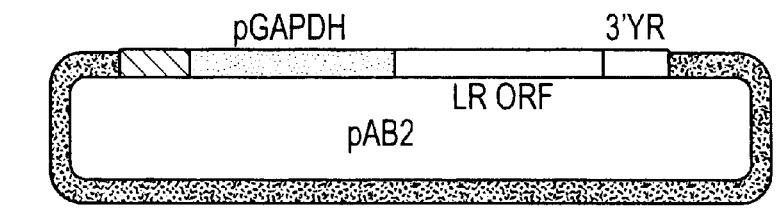

FIG. 9: construction of pAB2 from pUP81.

Figure 10:
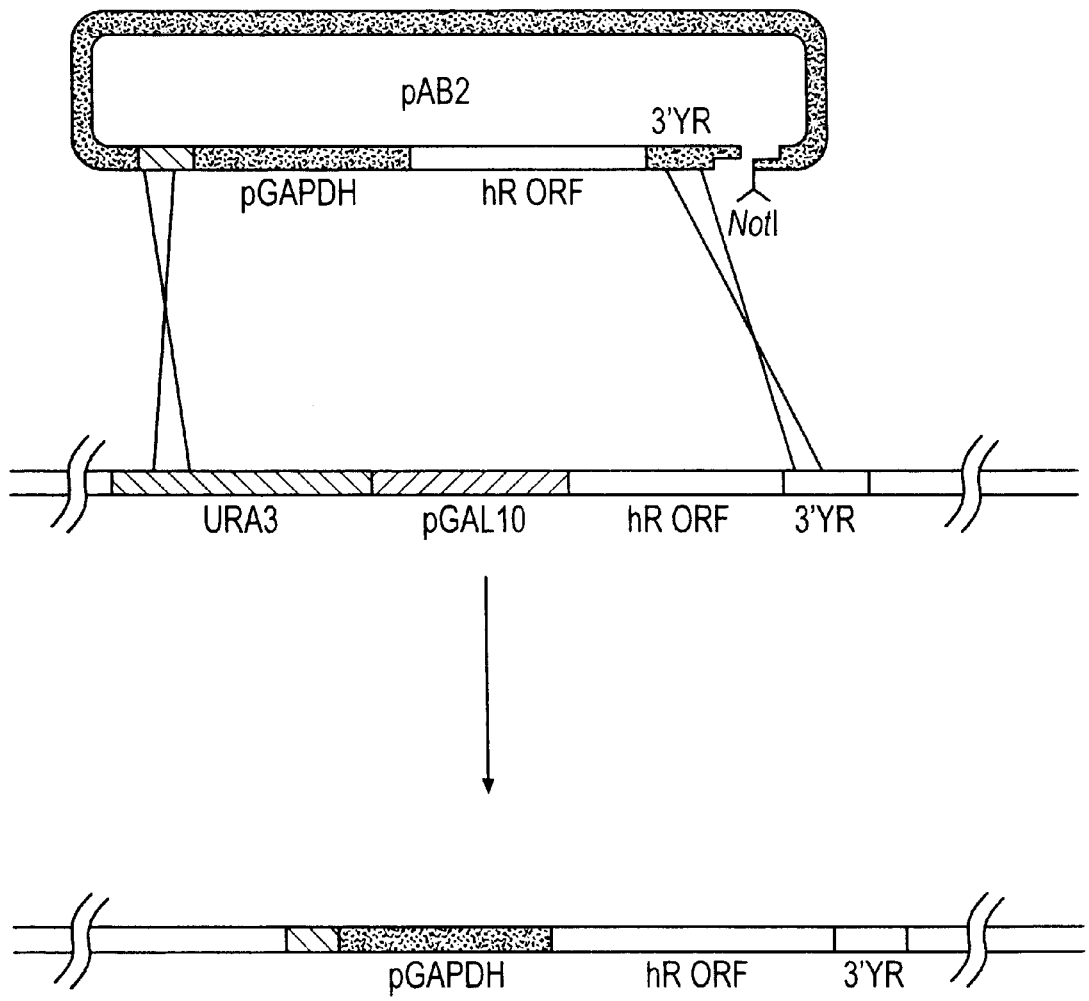

FIG. 10: construction of strain W(GhR,ΔB) using pAB2.

Figure 11:
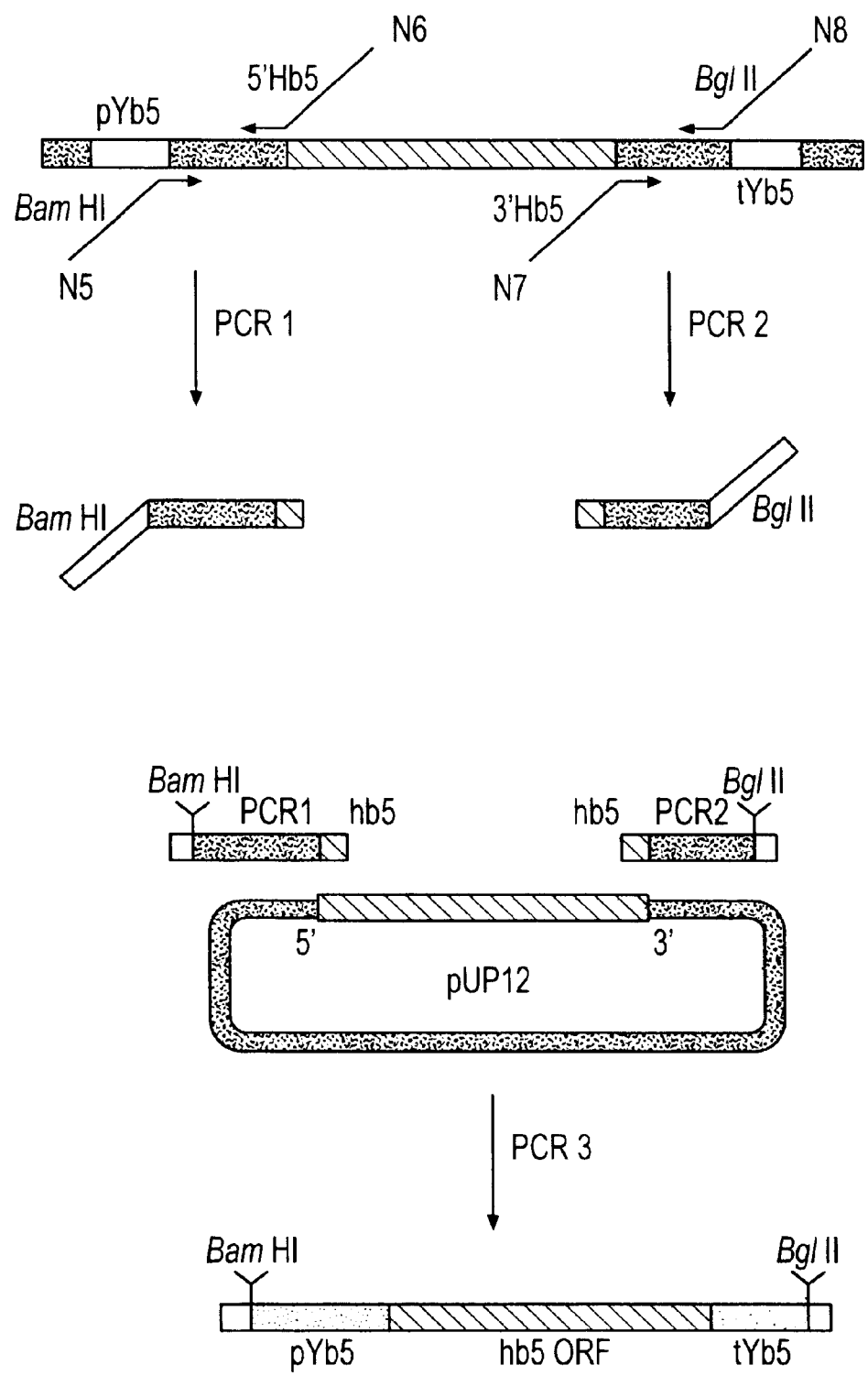

FIG. 11: construction of the hb5 cassette.

Figure 12:
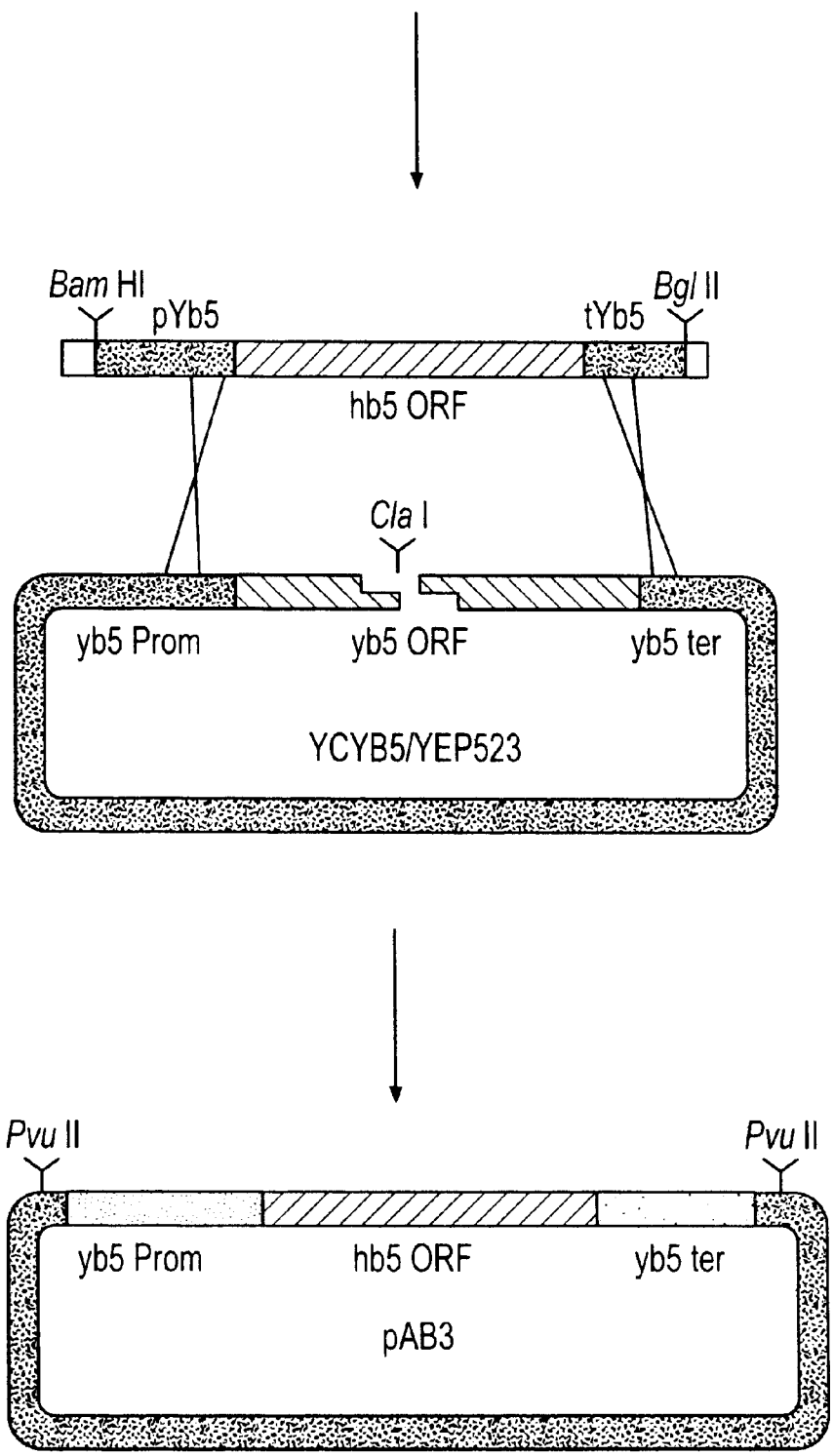

FIG. 12: construction of pAB3.

Figure 13:
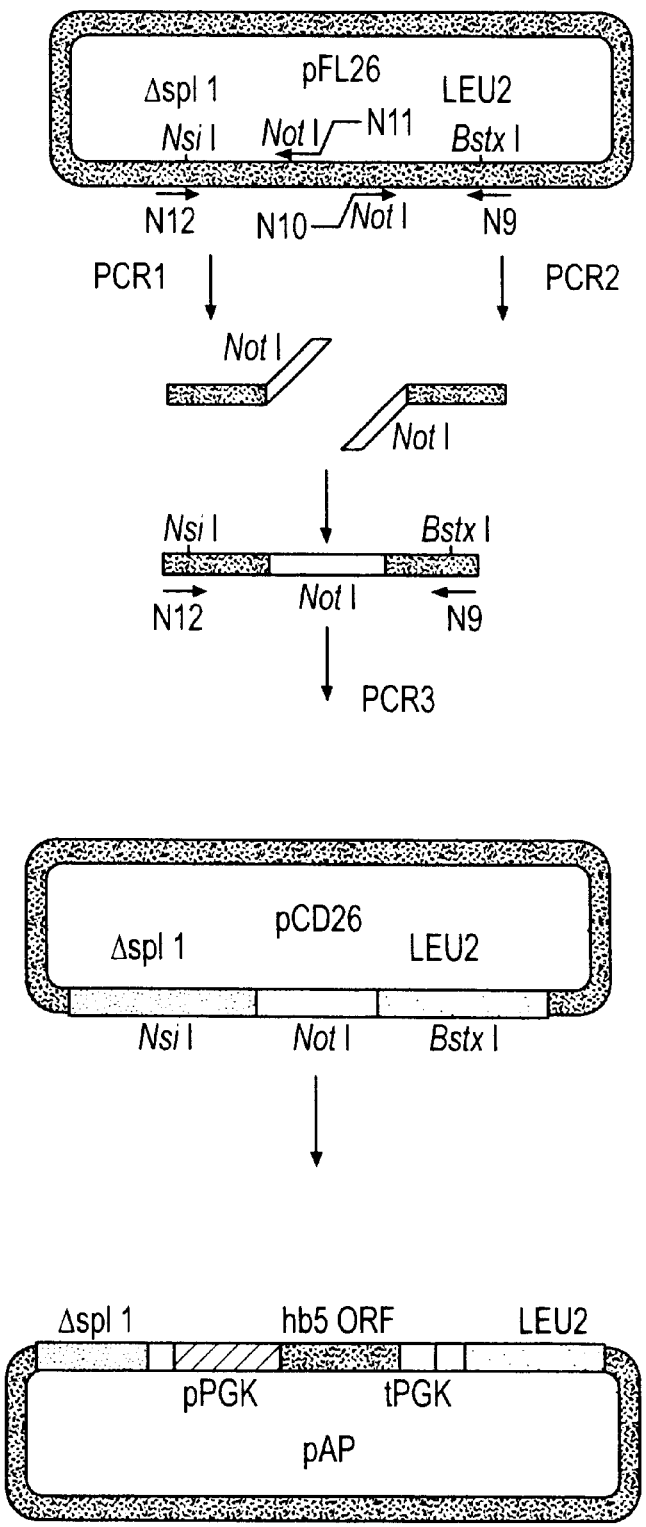
Figure 14:
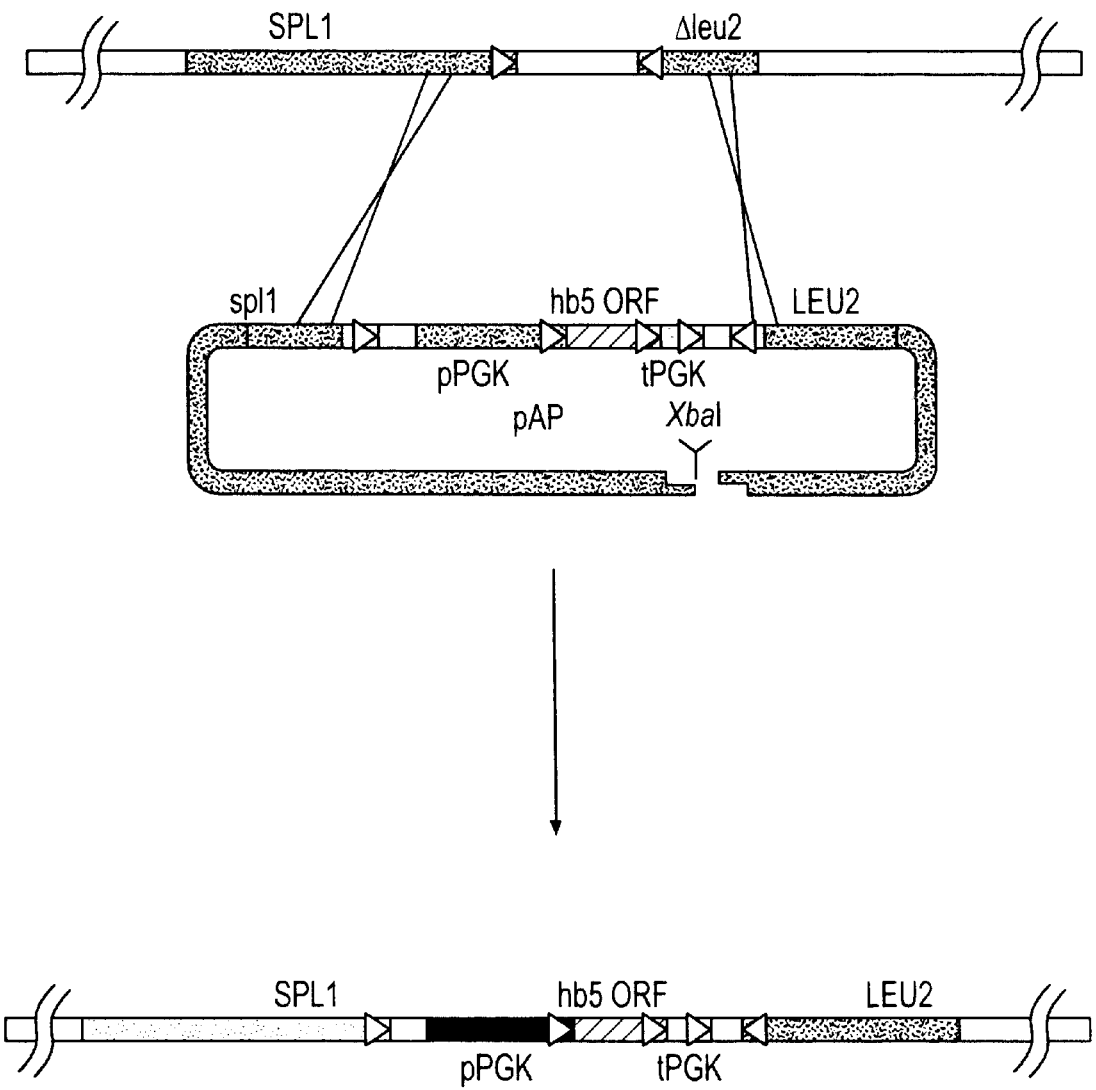

FIG. 13: construction of pAP1.

FIG. 14: construction of strain W(GhR,Lhb5).

Figure 15:
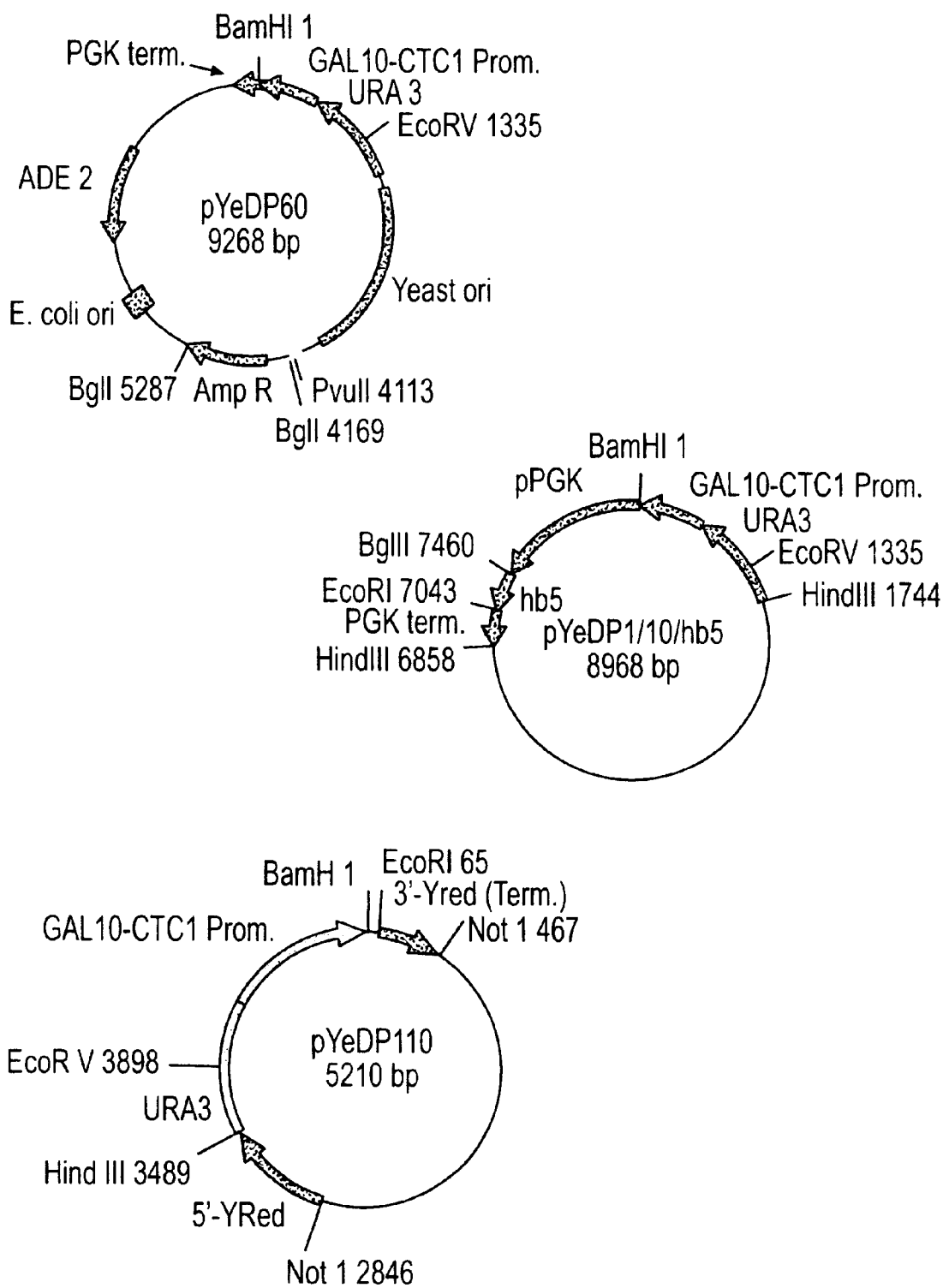

FIG. 15: depiction of plasmids pYeDP60, pYeDP1/10/hb5 and pYeDP110.

Figure 16:
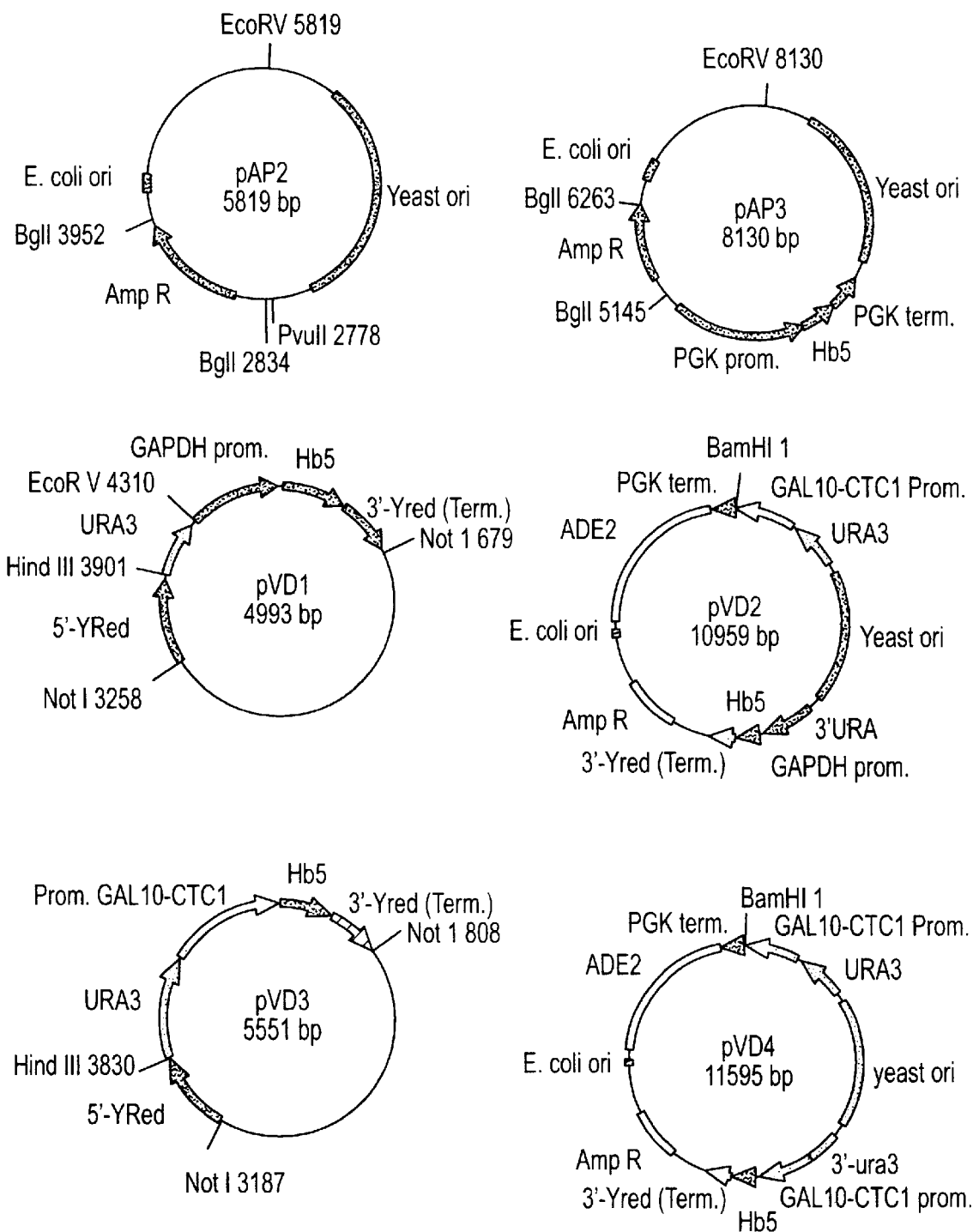

FIG. 16: depiction of plasmids pAP2, pAP3, pVD1, pVD2, pVD3 and pVD4.

Figure 17:
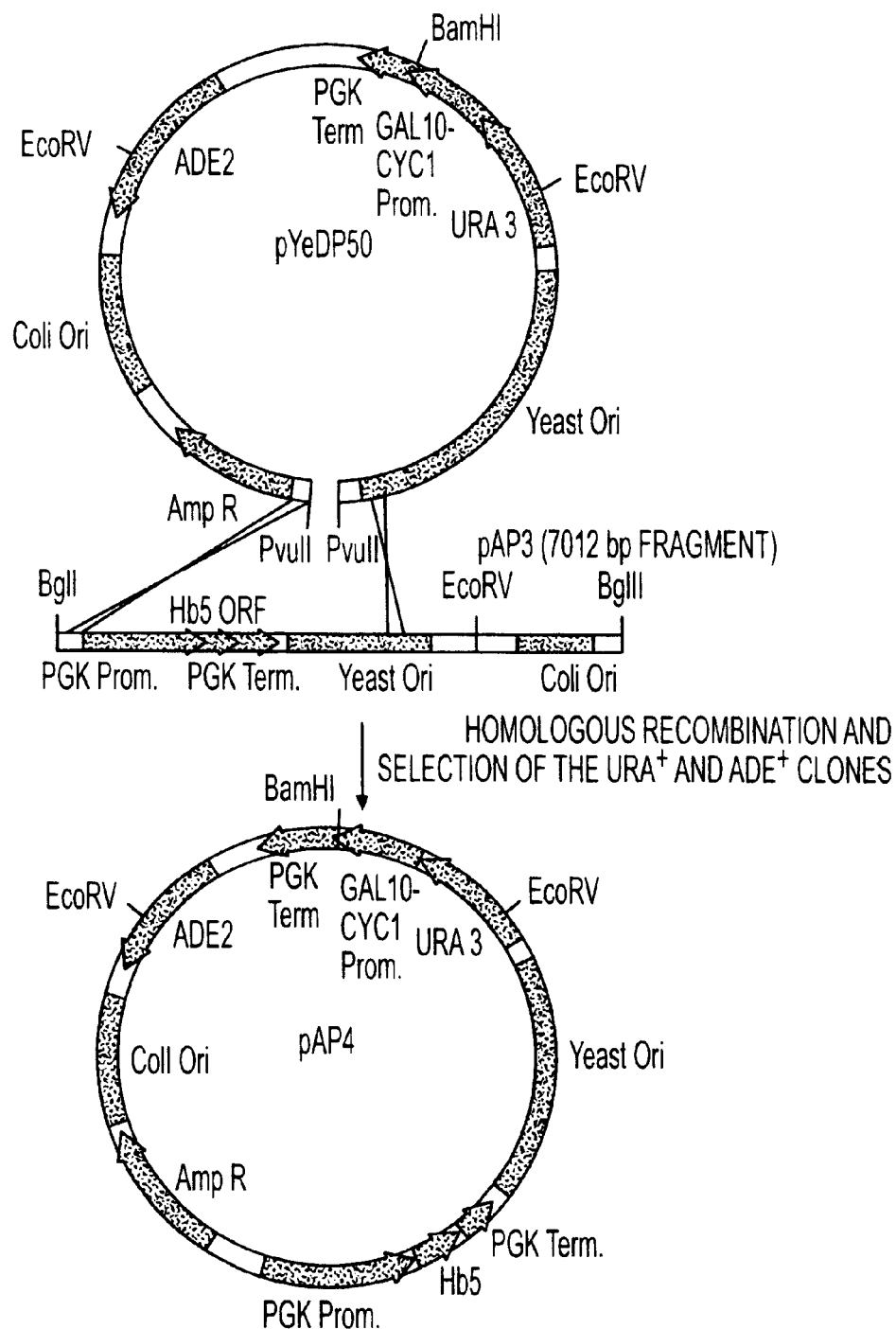

FIG. 17: construction and structure of pAP4.

Figure 18:
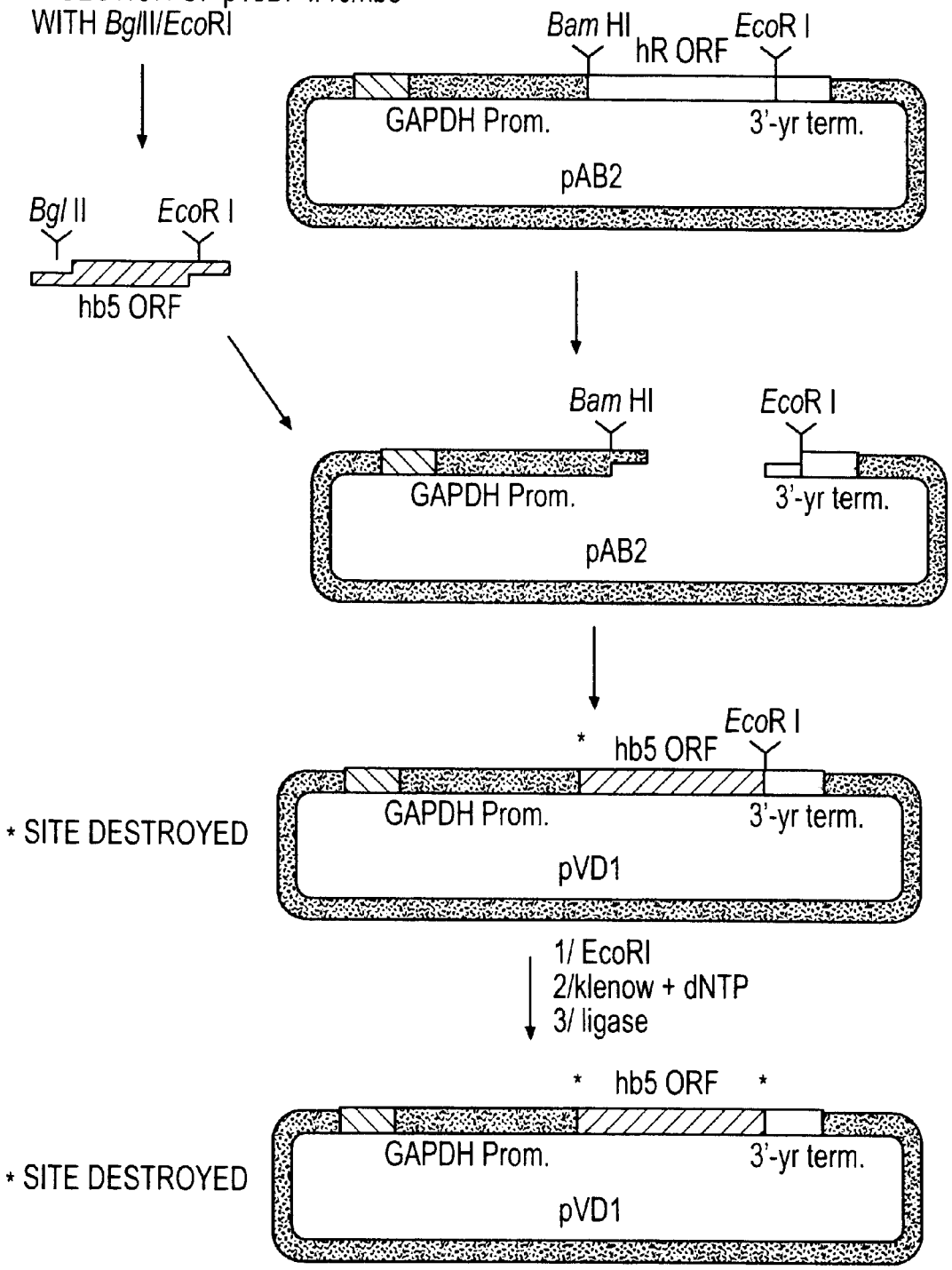

FIG. 18: construction of pVD1.

Figure 19:
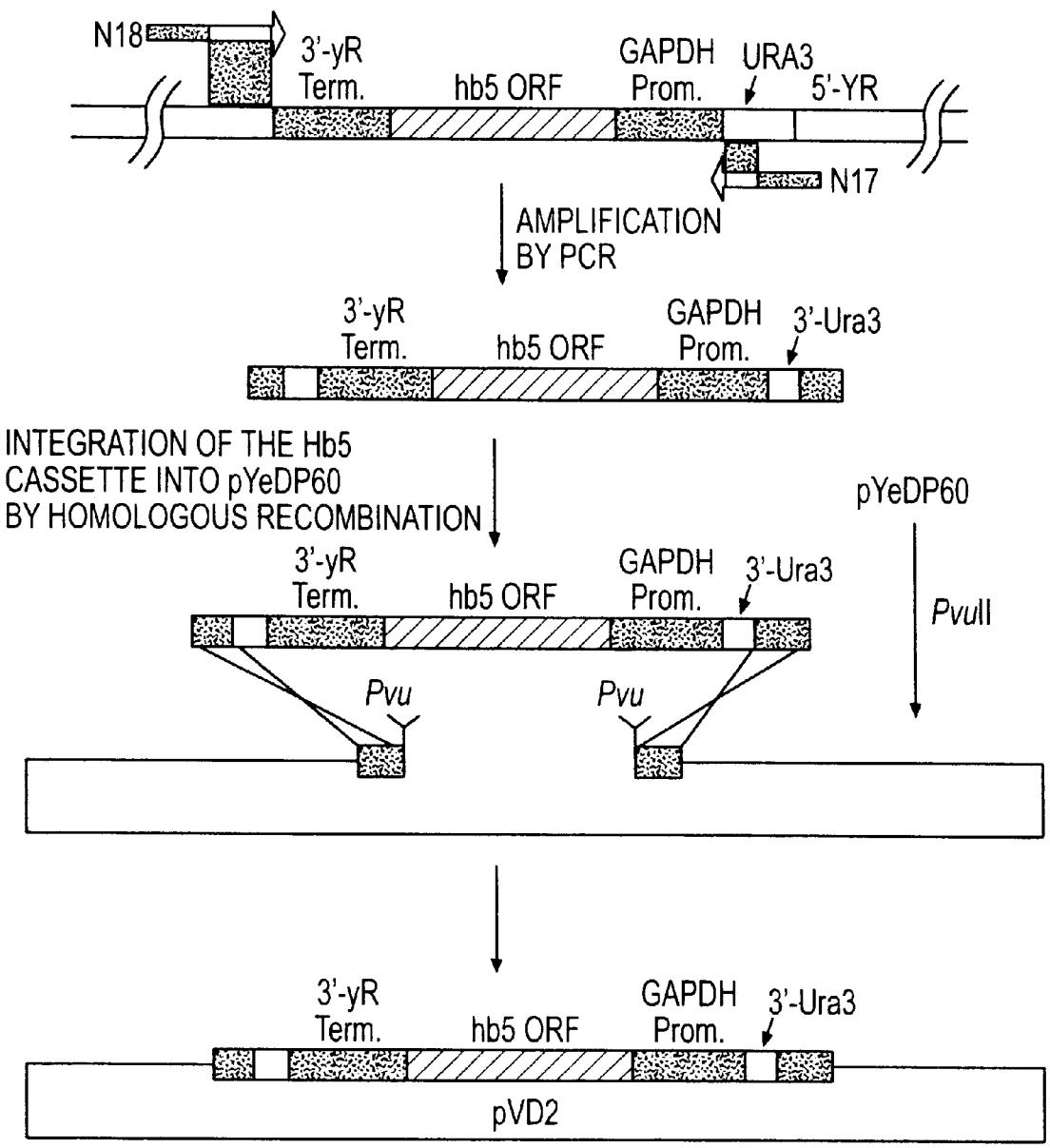

FIG. 19: construction of pVD2.

Figure 20:
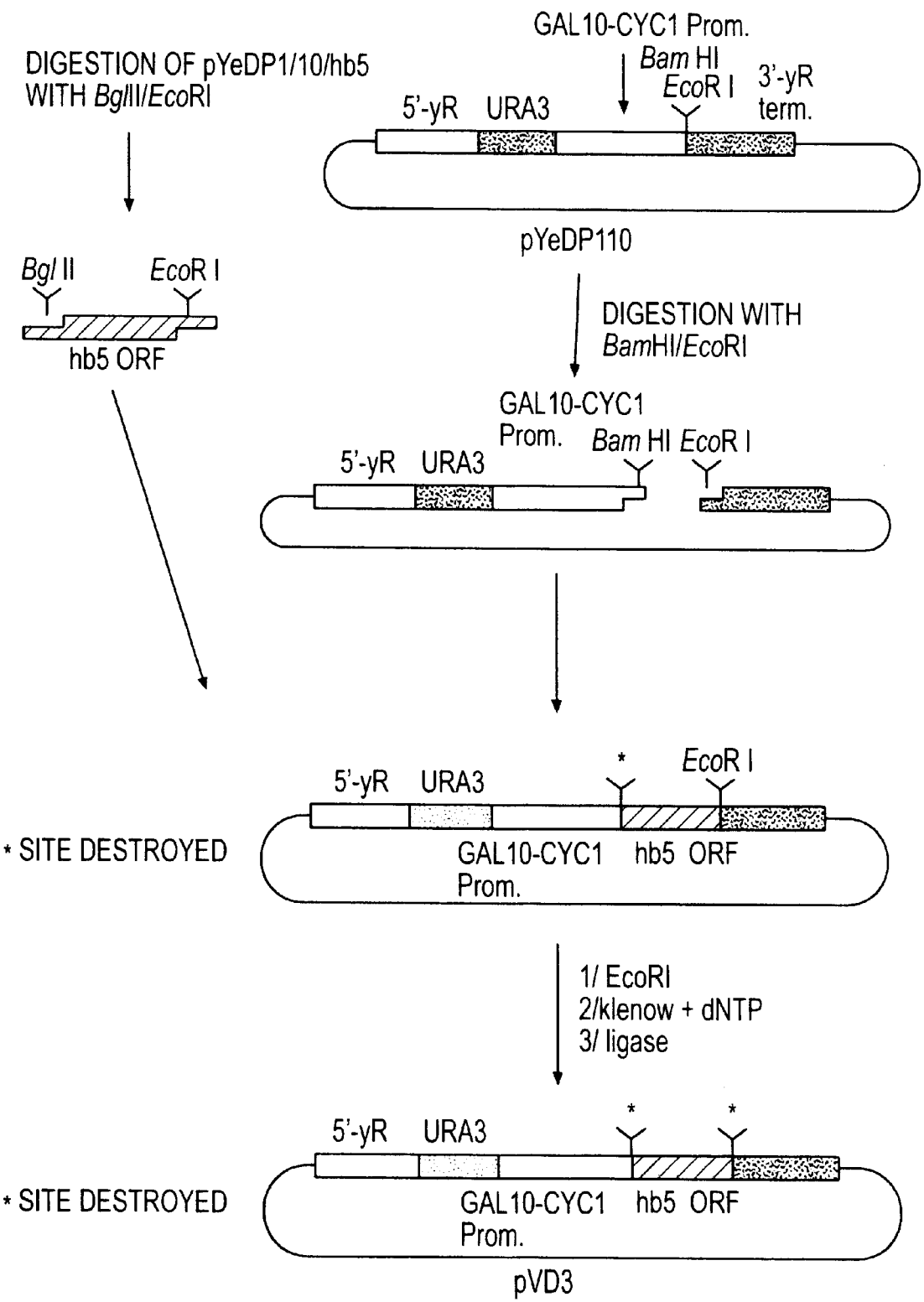

FIG. 20: construction of pVD3.

MATERIALS AND METHODS

1—Media

See Table I on the following page.

TABLE I

| | W0ADIF | W0ABIF | W0AIF | W0AI | YPGA | YPGa1A | N3 | Sporulation |
|---|---|---|---|---|---|---|---|---|
| YNB (1) | 1.43 g/l | 1.43 g/l | 1.43 g/l | 1.43 g/l | | | | |
| YE | | | | | 10 g/l | 10 g/l | 10 g/l | 2.5 g/l |
| B. peptone | | | | | 10 g/l | 10 g/l | 10 g/l | |
| Ammonium sulphate | 5 g/l | 5 g/l | 5 g/l | 5 g/l | | | | |
| Potassium acetate | | | | | | | | 20 g/l |
| German agar | 17 g/l | 17 g/l | 17 g/l | 17 g/l | 17 g/l | 17 g/l | 17 g/l | 17 g/l |
| D-Glucose | 20 g/l | 20 g/l | 20 g/l | 20 g/l | 20 g/l | | | |
| D-Galactose | | | | | | 20 g/l | | |
| Glycerol | | | | | | | 20 ml/l | |
| Adenine | 20 mg/l | 20 mg/l | 20 mg/l | 15 mg/l | 30 mg/l | | | |
| L-Histidine | 10 mg/l | | | | | | | |
| L-Leucine | 60 mg/l | 60 mg/l | 60 mg/l | | | | | |
| Tryptophan | 20 mg/l | 20 mg/l | 20 mg/l | 20 mg/l | | | | |
| Uracil | | 20 mg/l | | | | | | |

The sporulation medium is supplemented so as to complement the different auxotrophies depending on the strains.

(1) The yeast nitrogen base (YNB) without aminoacids and without ammonium is from GIBCO BRL. The ammonium sulphate is from MERCK. The German agar is from ROHSTOFF GmbH. The adenine, the L-histidine and the L-tryptophan are from SIGMA. The L-leucine and the uracil are from CALBIOCHEM. The D-glucose, the D-galactose, the glycerol and the anhydrous potassium acetate are from PROLABO. The bactopeptone (B. peptone) and the yeast extract (YE) are from DIFCO.

The N3 is buffered with a pH 6.2 phosphate buffer which is obtained by dissolving 89 g of $Na_2HPO_4$, 272 g of $KH_2PO_4$ and 1 g of specilline in 5 l of water.

The liquid media have the same composition as the solid media except that they do not contain any agar.

Ringer's solution: 0.9% NaCl in water.

2—Strains

Yeast: *S. cerevisiae*:

W(N): MATa and a, leu2-3,112, his3-11, ade2-1, trp1-1, ura3-1. W(N)a refers to W(N) Mat a and W(N)a refers to W(N) Mat a.

W(ΔB): MATa and a, leu2-3,112, ade2-1, trp1-1, ura3-1, Yb5: HIS3. W(ΔB)a refers to W(ΔB) Mat a and W(ΔB)a refers to W(ΔB) Mat a.

W(hR): MATa and a, leu2-3,112, his3-11, ade2-1, trp1-1, YRED: [GAL10-CYC1:: HRED]. W(hR)α refers to W(hR) Mat a and W(hR)a refers to W(hR) Mat a.

Bacterium:

E. coli DH5-1: supE44, hddR17, recA1, gyrA96, thi-1, relA1.

3—Vectors

Plasmid pUP81:

The sequence encoding the gene for human cytochrome P450 reductase, obtained by PCR using the primers N1 and N2, is cut with BamH1 and BglII and then cloned into the BamH1 site of the integration vector DPL110, with the ATG being alongside the GAL10-CYC1 promoter (Urban et al., 1993).

Primer N1:

5'-GCggatccATGGGAGACAGTCACGTGG-3' (SEQ ID No.1), in which bases 1 to 2 form a GC clamp, bases 3 to 8 (lower case letters) correspond to the added BamH1 site, bases 9 to 17 and 21 to 27 are, respectively, homologous to nucleotides 1 to 9 and 13 to 19 of the sequence of the open reading frame of the human reductase gene, while bases 18 to 20 (in bold letters) make it possible to mutate nucleotides TCC in positions 10 to 12 starting with the ATG of the sequence encoding the human reductase. This mutation destroys the fork structure of the RNA which is transcribed in the first 20 base pairs and which is responsible for inhibiting translation in yeast (Baim et al., 1988).

Primer N2:

5'-CGgaattcAGATCTAGCTCCACACGTCCAGG-3' (SEQ ID No.2), in which bases 1 to 2 form a GC clamp, bases 3 to 8 (lower case letters) correspond to the EcoRI site, bases 9 to 14 (underlined letters) correspond to the BglII site, bases 14 to 16 (bold letters) correspond to the stop codon (complementary strand), and bases 13 to 31 are complementary t6 nucleotides 2018 to 2034 of the open reading frame of the gene for human reductase.

Plasmid pFL26 (Bonneaud et al., 1991).

Plasmid pPL100:

ADE2/pFL (Stotz & Linder).

The yeast ADE2 gene was modified for the purpose of constructing the pPL100 vector. The internal BglII site of the gene is destroyed by mutating the adenosine in position 593, starting with the ATG, to guanine. This mutation does not change either the amino acid sequence or the activity of the protein. A BglII site is introduced into the region situated 5' of the ADE2 gene, i.e. in position −373 starting from the initiation codon. The gene possesses a BglII site in position 1862 starting with the ATG. The 2241 bp BglII fragment is cloned into the BglII site of the vector pFL36 (Bonneaud et al., 1991).

The "Blue Script" Plasmid is Described in the pCR-Scrip™ SK(+) Cloning Kit (Stratagene).

4—Crossing

The haploid strains of opposite signs (a or α) are cultured separately in complete YPGA medium. The cells are then diluted in Ringer's solution to approximately $10^5$ cells/ml. A mixture of 500 ml of each of the two suspensions of haploid cells is prepared. 50 ml of suspension from the mixture are spread on solid YPGA medium. After 8 h of growth, the cells are subcloned onto a selective medium which only complements the auxotrophies which are present simultaneously in the two parents. This permits growth of the diploid derived from the crossing but not that of the original haploids. After two days of growth, the diploid clones which appear are repicked onto the same selective medium.

5—Sporulation

The diploid cells are repicked onto a solid sporulation medium which is complemented with the diploid auxotrophy markers. After 3 days of sporulation, the spores are dissected.

6—Dissection of the Spores

Bulk Technique:

The spores are diluted to $5.10^8$ cells/ml in water containing 100 mg/ml zymolyase 10,000 (Seikagaku Kogyo Co., Tokyo, Japan) in 1.5 ml Eppendorf tubes and then incubated at 28° C. for 30 min. An aliquot of 500 ml is centrifuged at 10,000 rpm for 1 min. The cell pellet is taken up in 1 ml of water then centrifuged and taken up in 100 ml of water. The cells are vortexed for 2 min. The tube is rinsed with water by inverting it 2 to 3 times. After 5 rinses, the spores, which are hydrophobic, adhere to the walls of the tube while the vegetative diploid cells remain in suspension and are removed by rinsing. The spores are then resuspended in a 0.01% (v/v) solution of Nonidet P-40 (Sigma). The detergent is removed after centrifugation. The purified spores are taken up in Ringer's solution and spread on solid selective medium.

Microdissection:

The spores are incubated in a solution (containing 55% glycerol) of 0.5 g/l cytohelicase (Biosepra) at 22° C. for 15 min and then spread on a piece of agar which has previously been cut and placed on a cover glass. The cover glass is then placed upside down on a microdissection chamber. The four spores which are contained in a tetrad are separated under the microscope using a micromanipulator. The agar carrying the tetrads which have been thus dissected is placed on a dish on complete YPGalA medium.

7—Cloning the GAPDH Promoter

Amplification by PCR:

The PCR technique, using 50 ng of the primers N3 (SEQ ID No. 3) and N4 (SEQ ID No. 4) (FIG. 9) as primer, was employed to clone the DNA of the promoter of the gene for yeast glyceraldehyde phosphodehydrogenase from 100 ng of S. cerevisiae W(N) genomic DNA, which was prepared in accordance with the method described by Bellamine et al., 1994. The amplification was carried out using 2.5 U of native Pfu DNA polymerase (Stratagene). The polymerization reaction took place in 50 ml of a solution containing 20 mM Tris-HCl, 10 mM KCl, 6 mM $(NH_4)_2SO_4$, 2 mM $MgCl_2$, 0.1% Triton X-100, 10 mg/ml serum albumin without nuclease, and 200 mM of each of the four deoxynucleotide triphosphates (dNTP). The PCR conditions are as follows:

| 2 precycles: | 95° C. | 10 sec |
|---|---|---|
|  | 40° C. | 50 sec |
|  | 60° C. | 5 sec |
|  | 74° C. | 2 min |
| 25 cycles: | 95° C. | 5 sec |
|  | 48° C. | 50 sec |
|  | 65° C. | 5 sec |
|  | 74° C. | 2 min |

The Primer Sequences are

Primer N3:

5'-ccaagcttGAGTTTATCATTATCAATACTCG-3' (SEQ ID No. 3), in which the first two bases form a GC clamp, the lower case letters correspond to the HindIII site, and bases 9 to 31 are homologous with nucleotides −673 to −650 of the sequence of the promoter of the GAPDH gene.

Primer N4:

5'-CggatccTATTTATGTGTGTTTATTCGAAACTAAG TTCTTGG-3' (SEQ ID No. 4), in which the lower case letters correspond to the BamHI site, and bases 8 to 42 are complementary to nucleotides −6 to −48.

The size of the amplified DNA is 691 bp.

26 ml of 7.5 M ammonium acetate and 4 ml of water are added to 50 ml of the PCR product. The mixture is precipitated with 80 ml of ethanol at 22° C. for 10 min. The precipitated DNA is centrifuged at 10,000 rpm for 10 min. The pellet is washed with 70% (v/v) ethanol, dried and taken up in 20 ml of water.

An aliquot of 10 ng of this DNA is cloned into the SrfI site of the Blue Script vector belonging to the pCR-Script™ SK(+) cloning kit, in accordance with the recommendations of the vendor (Stratagene). The clones are sorted by restricting them with PvuII. Those which give PvuII fragments of 2513 and 1139 bp are sequenced through 100 bp at the site of the junction between the cloned DNA and the Blue Script vector using the Sequenase Version 2.0 DNA sequencing kit U.S.B. (Amersham). These constructs are termed pAB1.

Cloning the GAPDH Promoter Into the Integration Vector pUB81:

The pAB1 clone is cut with HindIII. This cleavage generates a sticky end site which is filled using the DNA polymerase Klenow fragment (Biolabs). The pAB1 vector, which has thus been linearized (fragment of 3652 bp), is then cut, at its 5' end, with BamHI and subsequently cloned into the pUP81 vector between the EcoRV and BamHI sites. During the ligation, the HindIII site, which has been rendered blunt-ended, attaches to the EcoRV site, which is blunt-ended, while the two BamHI half sites of the pGAPDH fragment and the pUP81 integration vector bind to each other. The EcoRV site was chosen for the purpose of disrupting the gene URA3 at the same time (FIG. 9). The clones are sorted by enzyme restriction with the enzymes PstI and BamHI. Those clones which give DNA fragments of 600 and 800 bp in addition to the fragments of 60, 104, 197, 385, 440 and 2564 bp (fragments which exist in the pUB81 vector) represent the pUP81 vectors which contain the DNA of the GAPDH promoter. This construct is termed pAB2. Three clones containing the pAB2 plasmid are verified by sequencing through 100 bp from the 5' end of the DNA of the promoter of the GAPDH gene using the primer N3 (SEQ ID No. 3).

8—Construction of the Cassette for Integrating Human Cytochrome b5 into the YCYB5 Locus This construction was carried out in three different PCR procedures.

In the first PCR (PCR 1), the 353 bp of the 3' end of the promoter of the gene for yeast cytochrome b5 (Yb5) were amplified using the primers N5 (SEQ ID No. 5) and N6 (SEQ ID No. 6) and W(N) yeast genomic DNA:

Primer N5:

5'-ggatccGAGCGGGTAATAGCCTGGAGTTTCC-3' (SEQ ID No. 5), comprises a BamHI site starting from its 5' end (in lower case letters). Bases 7 to 31 of this primer are homologous to nucleotides −331 to −306 of the open reading frame of the promoter of the gene for yeast cytochrome b5.

Primer N6:

5'-ccgactgctctgccatGATTGTTTGATATTTTATGTTGT AGTTGATTG-3' (SEQ ID No. 6), comprises, starting from its 5' end: bases 1 to 16 which represent the complementary sequence to the first 16 nucleotides of the 5' end of the open reading frame of the human cytochrome b5 gene (lower case letters), while bases 17 to 49 represent the complementary sequence to nucleotides −1 to −32 of the promoter of the gene for yeast cytochrome b5.

The size of the amplied fragment is 375 bp.

In the second PCR (PCR 2), the last 147 bp of the 5' part of the terminator of the yeast cytochrome b5 gene were amplified using the primers N7 (SEQ ID No. 7) and N8 (SEQ ID No. 8):

Primer N7:

5'-cctatacatggcagaggactgaATTCTTTTTCTTCCAGAA TAGCCCACAC-3' (SEQ ID No. 7), comprises, starting from its 5' end: bases 1 to 22: sequence which is homologous to nucleotides 383 to 405 of the open reading frame of the human cytochrome b5 gene (lower case letters), and bases 23 to 50, which is the homologous sequence to nucleotides 1 to 28 of the terminator starting from the stop codon.

Primer N8:

5'-GGagatctGTGACATACTTCTATGCGATATAG-3' (SEQ ID No. 8), comprises a GC clamp in bases 1 and 2, and a BglII site from base 3 to base 8 (in lower case letters). This primer is complementary, from base 9 to base 32, to nucleotides 1 to 147 of the open reading frame of the terminator of the yeast YCYB5 gene starting from the stop codon.

The size of the amplified fragment is 180 bp.

In FCR procedures 1 and 2, the genomic DNA of yeast W(N) is used as the template.

In a third PCR (PCR 3), 4 Primers are Used:

Two hundred nanograms of the products of the first two PCR procedures (375 and 180 bp) are used as primers, and 100 ng of DNA encompassing the coding sequence for human cytochrome b5 are used as the template (FIG. 11). While this gives rise to the cassette for integrating human b5 (CIH), the quantity produced is low.

The product of this PCR is then amplified using the primers N5 (SEQ ID No. 5) and N8 (SEQ ID No. 8), resulting in the production of the integration cassette in larger quantity. After amplification with the Pfu polymerase in the presence of 0.2 mM DNTP, the fusion product is treated at 76° C. for 30 min. The size of the resulting fragment is 917 bp. The amplifications are carried out using Taq polymerase (Appligene).

The Following PCR Programmes are Employed:

| PCR 1 and PCR 2: | | |
| --- | --- | --- |
| 2 precycles | 88° C. | 3 sec |
| | 95° C. | 10 sec |
| | 42° C. | 2 min |
| | 60° C. | 3 sec |
| | 74° C. | 2 min 30 sec |
| 30 cycles | 88° C. | 3 sec |
| | 95° C. | 5 sec |
| | 50° C. | 1 min |
| | 65° C. | 3 sec |
| | 74° C. | 2 min |
| PCR 3: | | |
| 3 precycles | 88° C. | 3 sec |
| | 95° C. | 10 sec |
| | 40° C. | 5 min |
| | 60° C. | 3 sec |
| | 74° C. | 3 min |
| 15 cycles | 88° C. | 3 sec |
| | 95° C. | 5 sec |
| | 45° C. | 2 min |
| | 65° C. | 3 sec |
| | 74° C. | 2 min |

The integration cassette (CIH) which is thus constructed is cloned into the SfrI site of the vector pCRScript. The clone which is obtained, i.e. pLIP1, is checked by sequencing through 200 bp at the two junctions: of the promoter and the terminator of the yeast YCYB5 gene and of the coding sequence of the human cytochrome b5 gene. In order to extend the bases for recombination to ensure that integration of the cassette for integrating the human b5 gene is effected correctly, a new integration cassette comprising the coding sequence of the human cytochrome b5 gene and the entire promoter and terminator of the yeast YCYB5 gene was constructed from the 917 bp BamHI/BglII fragment of the pLIP1 vector. Vector YCYB5/YEP352, which contains the whole of the yeast YCYB5 gene (Truan et al., 1994), is cut at a unique ClaI site. This linearized fragment is cotransformed into the W(N)a strain together with the 917 bp BamHI/BglII fragment of the pLIP1 vector. Since vector YCYB5/YEP352 is linearized within the coding sequence of the YCYB5 gene, the yeast cytochrome b5 will be replaced with the human cytochrome b5 following homologous recombination in the yeast (FIG. 12). The recombinants are selected on the basis of the recircularization of the expression vector (Bellamine et al., 1994). The new vector, i.e. pAB3, is recovered from the yeast and then amplified in the bacterium *E. coli* in accordance with the described method (Bellamine et al., 1994).

9—Construction of the Cassette for Integrating Human Cytochrome b5 into the Intergenic leu2D/SPL1 Site A cassette which makes it possible to integrate the human cytochrome b5 gene into the intergenic region, in the immediate vicinity of the LEU2 gene, using 500 bp of the SPL1 gene was constructed in two steps:

Construction of the vector pCD26: starting with the vector pFL26 (Bonneaud et al., 1991), which carries both the LEU2 gene and 500 bp of the SPL1 gene, a NotI site was introduced in three PCR procedures (FIG. 13).

In the first PCR, the 704 bp of the 3' part of the LEU2 gene are amplified using the primers N9 (SEQ ID No. 9) and N10 (SEQ ID No. 10):

Primer N9:

5'-TTGAAGGTTCAACATCAATTGATTG-3 (SEQ ID No. 9) is homologous with nucleotides 2190 to 2214 of the pFL26 vector, which nucleotides correspond to the end of the open reading frame of the LEU2 gene (in the pFL26 vector, the nucleotides are numbered starting with nucleotide 1, which is located 417 bp upstream of the BamHI site).

Primer N10:

5'-GTGTGgcggccgcCTCCTTGTCAATATTAATGTTA AAG-3' (SEQ ID No. 10), comprises, at its 5' end, five bases which are complementary to nucleotides 2890 to 2894 of the pFL26 vector, and then a NotI site, from base 6 to base 13, and a sequence which is complementary to nucleotides 2857 to 2881 from base 14 to base 38.

In the second PCR, the last 347 bp of the 3' part of the SPL1 gene are amplified using the primers N11 (SEQ ID No. 11) and N12 (SEQ ID No. 12):

Primer N11:

5'-CAAGGAGgcggccgcCACACAAAAAGTTAGGT GT-3' (SEQ ID No. 11), comprises, at its 5' end, seven bases which are complementary to nucleotides 2875 to 2881 of the sequence of the pFL26 vector, and then a NotI site from base 8 to base 15, and a sequence which is homologous to nucleotides 2889 to 2908 of pFL26 from base 16 to base 34.

Primer N12: 5'-TCTGCTTCCCTAGAACCTTCTTATG-3' (SEQ ID No. 12) is complementary to nucleotides 3198 to 3222 of the 3' end of the strand which encodes the open reading frame of the SPL1 gene in vector pFL26.

In the third PCR, 100 ng of the two fragments derived from the first two PCR procedures (having 20 bp of overlap containing the NotI site) are used as template, with the primers being N9 and N12. The 1031 bp which are amplified are cloned into the NsiI and BstXI sites of vector pFL26 to give vector pCD26.

The amplifications are carried out using Appligene Taq polymerase. The two first PCR procedures use the same programme as PCR procedures 1 and 2 of paragraph 8, while PCR 3 uses the following programme:

| 30 cycles | 95° C. | 10 sec |
|---|---|---|
| | 60° C. | 5 sec |
| | 45° C. | 1 min |
| | 65° C. | 5 sec |
| | 74° C. | 2 min |

Construction of the integration vector pAP1: The cassette for expressing human cytochrome b5 under the control of the promoter and the terminator of the yeast PGK (phosphoglycerate kinase) gene is recovered from plasmid pUP12, which was previously constructed (Urban et al., 1990), by means of cleaving it with BamHI and HindIII. This 2400 bp fragment is blunt-ended with mung bean nuclease (Biolaps) and then cloned into the pCD26 vector, which had been cut at the NotI site, with the cut ends being rendered blunt using the DNA polymerase Klenow fragment (FIG. 13). The clones which give PstI restriction fragments of 5154 and 2904 bp, which clones are given the designation pAP1, are used for the integration.

10—Vectors for Transforming with Cytochrome P450

The 9265 bp plasmid pYeDP60 is a shuttle vector (bacteria and yeast) which possesses the *E. coli* ora and 2 μ ori origins of replication, the bla gene, which encodes resistance to ampicillin, the URA3 and ADE2 genes, which are markers of auxotrophy complementations, a hybrid promoter, i.e. GAL10-CYC1, which is inducible in the presence of galactose, and the transcription terminator of the PGK gene. A polylinker comprising, inter alia, BamHI, KpnI and EcoRI restriction sites, is inserted between the promoter and the transcription terminator with the aim of cloning a cDNA to be expressed.

The plasmids 1A1/V60 and 3A4/V60 correspond to the vector V60 in which the coding sequences of the cDNAs encoding the human P450 cytochromes 1A1 and 3A4, respectively, have been inserted under the control of the GAL10-CYC1 promoter and the PGK transcription terminator.

11—Culture Medium for Transformation of the Yeast Strains

YPGE medium

| yeast extract | 10 g/l |
|---|---|
| bactopeptone | 10 g/l |
| glucose | 5 g/l |
| ethanol | 30 ml/l |

SW6 medium:

| yeast nitrogen base (Difco) | 7 g/l |
|---|---|
| glucose | 20 g/l |

-continued

| | |
|---|---|
| casamino acids (Difco) | 1 g/l |
| tryptophan | 20 mg/l |
| agar | 15 g/l (only for the solid media). |

For the corresponding galactose medium (SW5), the glucose is replaced with galactose at the same concentration.

12—Preparations of Microsomal Fractions 12.1 Transformation

The yeasts are transformed with plasmids 1A1/V60 or 3A4/V60 using the standard lithium chloride method. The transformants are selected on a synthetic yeast culture medium containing glucose and lacking adenine and uracil (SW6), to which are added the nutrients which are required to complement the residual auxotrophies depending on the strain employed (see strain genotypes). A large proportion of the primary transformants which are selected on the glucose medium do not grow on a minimum culture medium containing galactose. Only the clones which develop correctly on the galactose medium are retained.

12.2 Preculture:

The selected clones are repicked onto a non-inducing minimxum medium which contains glucose and which is selective for the plasmid (usually medium SW6) and then incubated overnight at 28° C. in 20 ml of the same liquid medium.

12.3 Culture:

250 ml of the YPGE medium are seeded with the preculture and incubated with shaking at 28° C. in order to obtain a cell density of between 8 and $9.6 \times 10^7$ cells/ml. Galactose is then added to a concentration of 20 g/l, and the culture is incubated at 28° C. overnight in order to obtain a cell density of $2 \times 10^8$ cells/ml. The presence of the galactose induces the cytochrome P450 and other genes which depend on the GAL10-CYC1 promoter.

12.4 Fractionation of the Cells:

The cells are centrifuged and washed in pH 7.4 TE buffer (50 mM Tris-HCl; 1 mM EDTA); 0.1 M KCl, and then resuspended in pH 7.4 TE buffer; 0.6 M sorbitol. In order to disrupt the cells, glass beads are added and the tubes are shaken vigorously from the bottom up for 5 min at 4° C. The following steps are then carried out at 4° C. The suspension of disrupted cells is recovered and the beads are washed several times with the same buffer. Two centrifugations of respectively 3 min at 3500 rpm and 10 min at 15,000 rpm are carried out in order to remove the cell debris, the nuclei and the mitochondrial fraction. In order to precipitate the microsomes, the supernatant is incubated in the presence of NaCl (0.15 M final concentration) and PEG 4000 (10% final concentration) in ice for 15 min. After a 10 min centrifugation at 10,000 rpm, the microsomal pellet is recovered in pH 7.4 TE buffer; 20% glycerol. The microsomal preparation is aliquoted and stored at −80° C.

13—Assaying the Cytochrome P450

The concentration of cytochrome P450 in the microsomal fractions is determined by spectrophotometry. The cytochrome P450 to be assayed is diluted in pH 7.4 TE buffer (approximately 1 mg of microsomal protein per ml), and reduced with a few grains of sodium dithionite. After the base line has been recorded (reduced cytochrome P450 against reduced cytochrome P450), a few bubbles of CO are added to the measurement cuvette and the difference spectrum is measured between 400 and 500 nm. The CO forms a stable complex with the reduced iron of the cytochrome P450, with this complex exhibiting a characteristic absorption maximum at 450 nm. The absorption coefficient, i.e. $\epsilon M$ (450–490 nm), is 91 $mM^{-1}.cm^{-1}$.

14—Assay of Microsomal Proteins

Total protein is assayed with the PIERCE-BCA assay kit under the conditions given by the manufacturer. Bovine serum albumin is used as the standard.

15—Catalytic Activities of the P450 Cytochromes 15.1 EROD Activity Tests on Microsomes The P450 cytochrome 1A1 catalyses the O-deethylation of 7-ethoxyresorufin. The product of the reaction, i.e. resorufin (7-hydroxyphenoxazine), fluoresces at 586 nm after excitation at 530 nm. The quantity of resorufin formed per unit time corresponds to the rate of resorufin accumulation.

The incubation mixture comprises:

2 $\mu$l of a microsomal suspension (between 20 and 50 $\mu$g of microsomal protein) in 1 ml of pH 7.4 TE buffer containing 50 $\mu$M NADPH and 2.5 $\mu$M 7-ethoxyresorufin. In order to determin the effect of rabbit cytochrome b5 on catalytic efficacy, the microsomal fractions are subjected to prior incubation in the cold in the presence of an excess of purified cytochrome.

15.2 THL Activity Test on Microsomes:

6β-hydroxylation of Testosterone

Testosterone is a steroid hormone which is hydroxylated in the 6β position by cytochrome 3A4. The incubation medium comprises 100 $\mu$g of microsomal protein in 0.25 ml of 50 mM Tris buffer, 1 mM EDTA, pH 7.4, or 50 mM sodium phosphate, pH 7.4, containing 50 $\mu$M NADPH and 80 $\mu$M testosterone (obtained from a 5 Mm stock solution in ethanol), in the absence or presence of an excess of cytochrome b5.

The incubations take place at 28° C. or 37° C. for 10 min. The reaction is stopped by adding 10 $\mu$l of 50% TFA in water. The extraction procedure is as follows:

adding 500 $\mu$l of dichloromethane vortexing at maximum speed for 1 min centrifuging for 5 min at 10,000 rpm removing the upper aqueous phase evaporating the organic phase under a stream of nitrogen.

The dry residue is taken up in 20 $\mu$l of methanol, and 20 $\mu$l of water are then added. Half of this mixture is injected into a reverse phase SPHERI-5RP-18.5 $\mu$m (100×2.1 mm) HPLC column using acetonitrile, at 1 ml/min, as the eluent. The acetonitrile content of the elution gradient varies from 10% (vol/vol) at 1 min up to 60% at 8 min. Detection is effected at 254 nm. The elution times are 6 min 20s for β-hydroxytestosterone and 8 min for testosterone.

EXAMPLES

Example No. 1

Construction of Strain W(hR, ΔB ):

Strain W(ΔB)a (which grows on W0ABIF medium) and strain W(hR)a (which grows on W0ADIF medium) are crossed and the diploid is selected on W0AIF glucose medium. This medium is lethal for each of the haploids but not for the diploid, i.e. W(hR/YR, Yb5/ΔYb5). The diploid clones are subcloned on the same selective medium. After sporulation, the tetrads are dissected either by microdissection or by bulk dissection. The spores, which are cultured on YPGalA medium, are then repicked onto different selective media containing galactose as the carbon source in order to test the auxotrophies of the different spores. The yeast clones which grow on galactose medium and which are prototrophic for uracil and histidine correspond to the W(hR, ΔB) strain. These yeasts do not grow when galactose is replaced by glucose in the same medium since, under these conditions, the human reductase is not expressed. Since these strains are then deficient both in reductase and in yeast b5 (the gene for which has been disrupted), they do not grow because the double deficiency is lethal (Truan et al., 1994). Four clones are retained for the subsequent work: i.e. Sp1 and Sp2, which are obtained by microdissection, and C1 and C2, which are obtained by bulk dissection.

Example No. 2
Construction of the Strain W(GhR, ΔB):

The GAPDH promoter integration vector, pAB2, which is cut with NotI, is used to transform the strain W(hR, ΔB)a. The vector pPL100 is used as the cotransformation marker (from 10 to 15 ng of vector pPL100 DNA per 2 mg of vector pAB2 DNA). The transformants are selected on W0BDIF medium. The clones are subjected to 3 series of screenings:

Selection for auxotrophy for uracil: the transformants are repicked onto W0ABDIF medium, and then onto W0ADIF medium in order to find the clones which do not grow in the absence of uracil. The loss of the URA3 gene suggests that the GAPDH promoter has replaced the GAL10-CYC1 promoter, since integration of the GAPDH promoter in place of the GAL10-CYC1 promoter simultaneously inactivates the URA3 gene, which is upstream of the promoter. 25% of the transformants do not grow in the absence of uracil (FIG. 10).

The second selection: the resistance of the W(Ghr, ΔB) clones to ketoconazole was evaluated (Patent No. WO94/01564) in order to verify the activity of the human reductase expressed under the control of the GAPDH promoter. Three different clones are resistant to 20 mg of ketoconazole/ml, while the W(hR) strain, in which the human reductase is expressed under the control of the GAL10-CYC1 promoter, is only resistant to from 1 to 5 mg/ml under the same conditions.

Third selection: the reduction of cytochrome c by the reductase contained in the microsomal fractions of the three, clones studied is measured in order to assess the level at which the human reductase is expressed in the W(GhR, ΔB) strain (Truan et al., 1993). Depending on the culture conditions, the reduction of cytochrome c is from 1.5 to 3 times greater than in the case of the W(hR) strain.

Respiration test: the clones which are obtained are repicked onto solid N3 medium in order to test their respiratory phenotype. The three clones do not grow on N3. They therefore have the respiration-negative phenotype. In order to render them [respiration-positive], these strains are crossed with a strain, i.e. W(hR)a, which has a respiration-positive phenotype. The diploid which is obtained, i.e. W(GhR/hR, ΔB/Yb5), is selected on W0AIF medium. After sporulation and bulk dissection, the genomic DNA of the haploids is prepared and a PCR is then carried out on this DNA using the primers N13 (SEQ ID No. 13) and N14 (SEQ ID No. 14).
Primer N13:
    5'-CAGATCTGCATGCCTAAAGTTTACAGTTACC-3' (SEQ ID No. 13); bases 1 to 30 are homologous with 30 nucleotides of the 5' end of the open reading frame of the yeast YCYB5 gene.
Primer N14:
    5'-CGGATTCTGCAGTTATTCGTTCAACAAATAAT AAGCAACACC-3' (SEQ ID No. 14); bases 1 to 42 are complementary to nucleotides 321 to 363 of the strand encoding yeast b5.

Of the six clones analysed, three have an amplified band at 363 bp (the coding sequence of the yeast cytochrome b5 gene), while: the other three clones have a band at 2063 bp, which corresponds to the sum of the size of HIS3 gene (1700 bp) and the size of the open reading frame of the yeast b5 (363 bp). These clones are subcloned onto solid W0ABIF medium in order to test their-atixotrophy in relation to histidine. All the clones grow in the absence of histidine whereas 50% of them (those which have the amplified PCR band of 363 bp) are supposed to be auxotrophic for histidine. The his3-11 gene is mutated in the original strain W(N). During the construction of strain W(ΔB) (Truan et al., 1993), disruption of the yeast YCYB5 gene by integration of the HIS3 gene into the YCYB5 coding sequence is probably accompanied by a second integration of the HIS3 gene at another locus. This would have led to the construction of a (W(ΔB)) strain which contains two functional copies of the HIS3 gene. Segregation of the HIS3 gene would not be more than the 2/2 type. This could explain the result which was obtained. Two of these clones (B1 and B2) are retained for the subsequent experiments.

Example No. 3
Construction of the Strain W(hR, hb5):

The 4 clones SP1, SP2, C1 and C2 are cultured in complete YPGalA liquid medium and transformed with the 2022 bp PvuII fragment from vector pAB3 (FIG. 12). The transformants are spread on YPGA medium. The integrants are selected on the basis of the ability of the human cytochrome b5 to enable strain W(hR, ΔB) to survive on glucose-containing medium. The clones which have grown are grouped together in batches. The genomic DNA of each batch is prepared. A PCR is carried out using the primers N5 (SEQ ID No. 5) and N15 (SEQ ID No. 15) (same conditions as for PCR procedures i and 2 of paragraph 8). The batches which give an amplified band of 758 bp are analysed individually by PCR. One clone which has integrated the human cytochrome b5 expression cassette into the YCYB5 locus, i.e. W(hR, hb5), is obtained from the initial clone W(hR, ΔB) Sp1.
Primer N15:
    5'-CCgaattcTGATCAGTCCTCTGCCATGTATAGG-3' (SEQ ID No. 15); bases 1 to 2 are a GC clamp, while bases 3 to 8 correspond to the EcoRI site (lower case letters), bases 9 to 14 correspond to the EclI site, bases 12 to 14 correspond to the stop codon and bases 15 to 33 are complementary to nucleotides 386 to 405 of the open reading frame of the human cytochrome b5 gene.

Example No. 4
Construction of the Strain W(GhR, hb5):

Clones B1 and B2 are cultured on complete liquid YPGA medium and transformed with the 2022 bp PvuII fragment of vector pAB3 and with vector pPL100 as the cotransformation marker. The transformants are selected on solid W0BDIF medium. The clones which grow are then grouped together in batches and analysed by PCR using the primers N3 (SEQ ID No. 3) and N13 (SEQ ID No. 13). The individual clones are verified by PCR in the same manner as in the previous paragraph.

Example No. 5
Construction of the Strain W(hR, Lhb5):

The integration vector pAP1 is cut with XbaI. The 4 clones SP1, SP2, C1 and C2 are transformed with this linearized fragment. The transformants are spread on YPGA medium. The cassette for expressing human cytochrome b5 under the control of the promoter and terminator of the PGK gene is integrated into the intergenic leu2/SPL1 site by means of homologous recombination in the yeast (FIG. 14). At the same time, this recombination replaces the inactive leu2-3 gene in the genome with wild-type LEU2, which is carried by the pAPI vector. The transformants are firstly selected for restitution of the LEU2 gene, that is for prototrophy of the transformants with regard to leucine (W0AI selection medium). A second selection is effected by carrying out a PCR on the genomic DNA of the transformants using the primers N9 (SEQ ID No. 9) and N16 (SEQ ID No. 16), and the-PCR conditions described in paragraph 9. The clones which exhibit a PCR band at 1495 bp have integrated the hb5 expression cassette.

Primer N16:

5'-GCCCAGATCTATGGCAGAGCAGTCGGACG-3' (SEQ ID No. 16), which comprises, from base 1 to base 4, a GC clamp sequence, from base 5 to base 10, a BglII site, and from base 11 to base 29 a sequence which is homologous to nucleotides 1 to 19 (starting from the ATG) of the open reading frame of the human cytochrome b5 gene.

Example No. 6
Construction of the Strain W(GhR, Lhb5):

This strain is constructed in the same way as for strain W(hr, Lhb5) except that W(GHR, ΔB) is used as the star ting strain. The transformants are selected directly on W0ABI medium and then by carrying out PCR analysis on the genomic DNA.

Example No. 7
Construction of the Strain W(R, Lhb5, Yb5):

Strain W(R) is cultured in complete liquid YGPA medium and transformed with vector pAP1, which has been linearized with XbaI. The transformants are firstly selected for restitution of the LEU2 gene, that is for the prototrophy of the transformants with regard to leucine (W0AI selection medium). A second selection is effected by means of PCR, which is carried out on the genomic DNA of the transformants using the primers N9 (SEQ ID No. 9) and N16 (SEQ ID No. 16) and the PCR conditions described in paragraph 9 (materials and methods). The clones which exhibit a PCR band of 1495 bp have integrated the hb5 expression cassette. This strain overexpresses yeast reductase in the presence of galactose and expresses human cytochrome b5 under the control of the PGK promoter. The expression of endogenous b5 is unchanged as compared with the normal strain.

Example No. 8
Construction of the Strain W(hR, Lhb5, Yb5):

The construction is identical to that for the strain W(R, Lhb5, Yb5) except that the strain W(R) is replaced with the strain W(hR).

Example No. 9

Level at which the P450 cytochromes are expressed in the yeast strains according to the invention.

The levels at which the two P450 cytochromes are expressed in the different strains are shown in Tables II and III. Surprisingly, the level at which the P450 cytochromes are expressed is significantly increased, under equivalent culture conditions, in the humanized strains. It is to be noted that the activity per mg of protein increased in proportion both to the level of expression and the turnover value.

TABLE II

Expression of the human cytochrome P450 1A1 in humanized yeast microsomes.

| Strains | P450 ($\mu$M) | Protein (mg/ml)[a] | P450 (pmol/mg)[b] |
|---|---|---|---|
| W(N) | 1.6 | 20 | 80 |
| W(R) | 4.5 | 30 | 150 |
| W(R, Lhb5, Yb5) | 4.1 | 31 | 130 |
| W(hR) | 4.4 | 28 | 155 |
| W(hR, Lhb5) | 5.6 | 22 | 260 |
| W(GhR, ΔB) | 6.6 | 26 | 250 |
| W(GhR, Lhb5) | 10.1 | 29.5 | 342 |

[a]concentration of cytochrome P450 (determined spectrophotometrically) in the microsomal suspension.
[b]concentration of total protein in the microsomal solution.

TABLE III

Expression of the human cytochrome P450 3A4 in humanized yeast microsomes.

| Strains | P450 ($\mu$M)[a] | Protein (mg/ml)[b] | P450 (pmol/mg) |
|---|---|---|---|
| W(N) | | | 80 |
| W(R) | 10.4 | 32 | 320 |
| W(R, Lhb5, Yb5) | 9.1 | 30 | 300 |
| W(hR) | 10.5 | 34 | 310 |
| W(hR, Lhb5) | 4 | 23 | 180 |
| W(GhR, ΔB) | 7.4 | 29 | 250 |
| W(GhR, Lhb5) | 9 | 22 | 410 |

[a]concentration of cytochrome P450 (determined spectrophotometrically) in the microsomal suspension.
[b]concentration of total protein in the microsomal solution.

Example No. 10 Effect of the reductase and the cytochrome b5 on the enzymatic characteristics of the P450 cytochromes 1A1 and 3A4 produced in yeast.

The results obtained indicate that the catalytic efficacy of the P450 cytochrome 1A1 is optimal in the haploid strain W(R, LHb5), which overproduces yeast reductase and produces human cytochrome b5. Nevertheless, the addition of rabbit cytochrome b5 produces a slight additional increase in the activity, which reaches a turnover 27 pmol of metabolite/pmol of cytochrome P450 per min.

Contrary to the results obtained with cytochrome P45 1A1, the catalytic efficacy of cytochrome P450 3A4 is preferentially increased in yeast strains which express the human reductase. The strain W(GhR, hb5) displays optimal catalytic efficacy. Whatever the nature and the level of the reductase, the presence of the cDNA encoding cytochrome b5 in the genome of the strains translates into an increase in catalytic efficacy (by a factor of from 2 to 20). Deletion of the endogenous cytochrome b5 gene appears to be a highly favourable factor, particularly when human b5 is expressed. Expression of the human reductase, disruption of the endogenous cytochrome b5 and expression of the human b5 in one and the same haploid yeast strain constitutes a combination which is particularly favourable for expressing certain human P450 cytochromes, in particular the P450 cytochrome 3A4.

Example 11

Construction of plasmids which permit coexpression of cytochrome P450 and human microsomal cytochrome b5.

This example describes the construction of plasmids which can be used to optimize the P450 activity of the yeast strains according to the invention. These plasmids enable a cytochrome P450 and human microsomal cytochrome b5 to be expressed simultaneously. All the plasmids of the series contain the original combination of the following common characteristics.
(i) The cassette for expressing the P450 is preferably under the transcriptional control of the inducible GAL10-CYC1 promoter.
(ii) The cassette for expressing the cytochrome b5 is preferably under the transcriptional control of one of the three following promoters: GAL10-CYC1, GAPDH or PGK.
(iii) Two selection markers are present, one of which is preferably the yeast ADE2 gene.
(iv) The two expression cassettes are separated on the plasmid by, on the one hand, the yeast origin of is replication and, on the other hand, the ADE2 marker.

When two identical promoters of the GAL10-CYC1 type are used for expressing the b5 and the P450, these promoters are in opposite orientations on the plasmid (with respect to one revolution of the plasmid). Two different transcription terminators are used, preferably those of the yeast PGK and yeast P450 reductase genes. The purpose of the combination of these properties is to obtain plasmids which are stable, in particular with respect to the phenomena of homologous recombination.

The plasmids of the series differ with regard to the nature of the promoter which is used for expressing the cytochrome b5. This property makes it possible to modulate the relative levels of expression and to optimize them for different culture conditions or different applications.

Example 11.1

Construction of plasmid pAP4, which enables a P450 to be expressed under the control of the GAL10-CYC1 promoter and human b5 to be expressed under the control of a PGK promoter.

The vector pYeDP1/10/Hb5, which is described in FIG. 15, contains the ORF (open reading frame) of the human cytochrome b5, with this ORF being flanked by a BglII site immediately upstream of the initiation codon and by an EcoRI site immediately downstream of the STOP codon. This is because the BglII/EcoRI cassette is included in the expression vector pYeDP1/10 (Cullin and Pompon, Gene. 65 (1988) 203–217). This vector is digested with BamHI and HindIII. The 2310 bp fragment, which contains the sequences of the promoter and the terminator of the PGK gene, and the sequence encoding the human cytochrome b5, is recovered and then treated with the DNA polymerase Klenow fragment in order to render its ends blunt. Vector pYeDP60 is digested with the restriction enzyme EcoRV and the 5819 bp fragment is recovered. This fragment contains the yeast and *E. coli* origins of replication. The fragment is recircularized on itself and gives rise to vector pAP2. This vector is digested with PvuII, and the 2310 bp fragment derived from the vector pYeDP1/10/Hb5 is inserted into it in the orientation which gives vector pAP3, whose expression cassette is as depicted in FIG. 17. This vector is digested with BglI. The 7012 bp fragment is recovered. Vector pYeDP60 is linearized with PvuII and the band which corresponds to the linearized plasmid is purified. A yeast culture derived from a clone of strain W(N) is cotransformed with the linear plasmid and the 7012 bp fragment, and clones which are prototrophic for uracil and adenine are selected. As a result of homologous recombination in the yeast, the cassette for expressing the cytochrome b5 under the control of the promoter and terminator of the PGK gene is substituted into the PvuII site of vector pYeDP60, resulting in the final vector pAP4 (FIGS. 16 and 17). The plasmid DNA corresponding to vector pAP4 is recovered from the yeast and used to transform *E. coli* (Ampr). Following selection, and after amplifying the plasmid and checking its structure by restriction digestion, the ORF of the cytochrome P450 of interest is inserted into vector pAP4 in the multiple cloning site which is located between the GAL10-CYC1 promoter and the PGK gene terminator. The resulting plasmid is used to transform, by means of selecting clones which are prototrophic for adenine and uracil, the receptor yeast strain, which is preferably selected from those described in the present patent.

Example 11.2

Construction of plasmid pVD2, which enables a P450 to be expressed under the control of the GAL10-CYC1 promoter and the human b5 to be expressed under the control of the GAPDH promoter.

The vector pYeDP1/10/Hb5 is digested with BglII and EcoRI in order to recover the band encoding human cytochrome b5. The 417 bp band corresponding to the b5 ORF is purified and then cloned into pAB2, which is digested with BamHI and EcoRI. The EcoRI site in the resulting vector is then destroyed by digesting with EcoRI and then filling in the site with the DNA polymerase Klenow fragment, after which the vector is recircularized with ligase. This 4993 bp plasmid is termed pVD1 (FIGS. 16 and 18).

The pVDI expression cassette is then amplified by PCR using the primers N17 (SEQ ID No. 17) and N18 (SEQ ID No. 18). The size of the amplified band is 1753 bp. The primers are designed to add tails for homologous recombination with the region situated around the unique PvuII site of pYeDP60 to the two ends of the expression cassette. The vector pVD2, as shown in FIGS. 16 and 19, is then obtained by homologous recombination (see Example 11.1. and FIG. 17) between pYeDP60, which is linearized at the PvuII site, and dephosphorylated with alkaline phosphatase, and the expression cassette, which has been amplified by PCR. The structure of pVD2 is verified by digestion with PstI and HindIII after it has been shuttled in yeast (cotransformation) and then *E. coli* (selection and amplification). The desired plasmid, which gives a digestion band at 10994 bp, is termed pVD2 (FIG. 19). The different junctions of the expression cassette are verified by sequencing using the primers N19 (SEQ ID No. 19) and N20 (SEQ ID No. 20).

Example 11.3

Construction of plasmid pVD3, which permits expression of a P450 under the control of the GAL10-CYC1 promoter and of human b5 under the control of a GAL10-CYC1 promoter.

As in the previous construction, the human cytochrome b5 ORF is obtained from pYeDP1/10/hb5 in the form of a BglII/EcoRI fragment. This ORF is introduced, by ligation, between the BamHI and EcoR1 sites of plasmid pYeDP110, which plasmid is described in FIG. 15 and contains a sequence segment consisting of (i) sequences situated immediately upstream of the promoter region of the yeast P450 reductase gene, (ii) the URA3 gene, (iii) the GAL10-CYC1 promoter and (iv) the transcription terminator of the yeast P450 reductase gene. As before, the EcoRI site in the plasmid resulting from the ligation is destroyed by cleavage/filling-in/ligation in order to yield a 5551 bp plasmid, which is termed pVD3 (FIG. 20). The cassette for expressing human cytochrome b5 under the GAL10-CYC1 promoter is then amplified by PCR using primers N17 and N18 in a similar manner to that described in Example 12. The amplified band of 2365 bp is purified and then introduced, as before, by homologous recombination at the PvuII site of pYeDP60 (as shown in FIG. 19 but replacing the GAPDH promoter with the GAL10-CYC1 promoter). The nature of the sequences of the recombination tails introduced by PCR ensures that the two GAL10-CYC1 cassettes which are present on the recombinant plasmid are in opposite orientations, as pointed out in the description of the general structure of the plasmids of the invention. The 11595 bp plasmid, which is termed pVD4 and is as shown in FIG. 16, is then selected after shuttling between yeast and E. coli. The junction between the GAL10-CYC1 promoter and the cytochrome b5 gene is verified by sequencing using the primer N21 (SEQ ID No. 21).

Nomenclature of the Resulting Strains:
W(GhR, ΔB): MATa, leu2-3, 112, ade2-1, trp1-1, ura3-1.
W(hR, ΔB): MATa, leu2-3, 112, ade2-1, trp1-1.
W(hR, hb5): MATa, leu2-3, 112, ade2-1, trp1-1.
W(GhR, hb5): MATA, leu2-3, 112, ade2-1, trp1-1, ura3-1.
W(hR, Lhb5): MATa, ade2-1, trp1-1.
W(GhR, Lhb5): MATa, ade2-1, trp1-1, ura3-1.
W(R, Lhb5, Yb5)
W(hR, Lhb5, Yb5)

Sequences of the Primers Employed:
(SEQ ID No. 1) N1: 5'GCGGATCCATGGGAGACAGT-CACGTGG3'.
(SEQ ID No. 2) N2: 5'-CGGAATTCAGATCTAGCTCCACACGTCCAGG-3'.
(SEQ ID No. 3) N3: 5'-CCAAGCTTGAGTTTATCATTATCAATACTCG-3'.
(SEQ ID No. 4) N4: 5'-CGGATCCTATTTATGTGTGTTTATTCGAAACTAAGTTCTTGG-3'.
(SEQ ID No. 5) N5: 5'-GGATCCGAGCGGGTAATAGCCTGGAGTTTCC-3'.
(SEQ ID No. 6) N6: 5'-CCGACTGCTCTGCCATGATTGTTTGATATTTTATGTTGTAGTTGATTG-3'.
(SEQ ID No. 7) N7: 5'-CCTATACATGGCAGGACTGAATTCTTTTTCTTCCAGAATAGCCCACAC-3'.
(SEQ ID No. 8) N8: 5'-GGAGATCTGTGACATACTTCTATGCGATATAG-3'.
(SEQ ID No. 9) N9: 5'-TTGAAGGTTCAACATCAATTGATTG-3'.
(SEQ ID No. 10) N10: 5'-GTGTGGCGGCCGCCTCCTTGTCAATATTAATGTTAAAG-3'.
(SEQ ID No. 11) N11: 5'-CAAGGAGGCGGCCGCCACACAAAAAGTTAGGTGT-3'.
(SEQ ID No. 12) N12: 5'-TCTGCTTCCCTAGAACCTTCTTATG-3'.
(SEQ ID No. 13) N13: 5'-CAGATCTGCATGCCTAAAGTTTACAGTTACC-3'.
(SEQ ID No. 14) N14: 3'-CGGATTCTGCAGTTATTCGTTCAACAAATAATAAGCAACACC-3'.
(SEQ ID No. 15) N15: 5'-CCGAATTCTGATCAGTCCTCTGCCATGTATAGG-3'.
(SEQ ID No. 16) N16: 5'-GCCCAGATCTATGGCAGAGCAGTCGGACG-3'.

(SEQ ID No. 17) N17: 5'-ggcgttacccaacttaatcgccttgcacatcccccttttcgccGGAACGTGCTGCTACTCATCCTAGTCC The first 42 bases are homologous to the region of pYeDP60 between bases 4069 and 4113. Bases 43–69, the nucleotides of the primer, which are in upper case, are homologous to the region of pUB81 between bases 5772 and 5799, which bases correspond to a region of the URA3 gene.

(SEQ ID No. 18) N18: 5'-gggaagggcgatcggtgcgggcctcttcgctattacgccagctGGCCGATTCATTAATGCAGCTGGGCGG The first 43 bases are homologous to the complementary strand of the region of pYeDP60 between bases 4114 and 4157. Bases 44 to 71 are homologous to the region of pUB81 between bases 2507 and 2538.

(SEQ ID No. 19) N19: 5'-ccccccttttcgccagggaacgtgc

This primer is homologous with the region of pVD2 between 4102 and 4125, corresponding to the end of the open reading frame of the URA3 gene which is adjacent to the cassette for integrating human cytochrome b5 under the control of the GAPDH promoter.

(SEQ ID No. 20) N20: 5'-cggtaggtattgattgtaattctg

This sequencing primer is homologous to the part of pVD2 between bases 4835 and 4860, which sequence corresponds to the end of the GAPDH promoter.

(SEQ ID No. 21) N21: 5'-ggcatgcatgtgctctgtatg

This sequencing primer is homologous to the region of the GAL10-CYC1 promoter which is situated at −120 bp from the junction between the GAL10-CYC1 promoter and the human cytochrome b5 ORF.

REFERENCES

Baim, S. B. & Scherman, F. (1988) mRNA structures influencing translation in the yeast S. cerevisae, Mol. Cell. Biol. 8, 1591–1601.

Barnes, H. J. Arlotto, M. P. & Waterman, M. R. (1991) Expression and enzymatic activity of recombinant cytochrome P450 17a-hydroxylase in Escherichia coli Proc. Natl. Acad. Sci. USA 88, 5597–5601.

Bellamine, A. Gautier, J. C. Urban, P. & Pompon, D. (1994) Chimeras of the human cytochrome P450 1A family produced in yeast: Accumulation in microsomal membranes, enzyme kinetics and stability, Eur. J. Biochem. 225, 1005–1013.

Bonneaud, N. Ozier-Kalogeropoulos, O. Li, G. Labrousse, M. Minvielle-Sebastia, L. & Lacroute, F. (1991) A family of low and high copy replicative, integrative and single strand S. cerevisiae/E. coli shuttle vectors, Yeast 7, 609–615.

Cullin, C. & Pompon, D. (1988) Synthesis of functional mouse cytochrome P450 P1 and chimeric cytochrome P450 P3-1 in the yeast Saccharomyces cerevisiae, Gene (Amst.) 65, 203–217.

Doehmer, J. & Greim, H. Cytochromes P450 in genetically engineered cell cultures: the gene technological approach in Cytochrome P450, Handbook of experimental pharmacology, 105; Eds Schenkman, J. B. & Greim, H. Springer-Verlag, Berlin, Heidelberg, New York (1992), 3–13.

Guengerich, F. P. (1988) Roles of cytochrome P450 enzymes in chemical carcinogenesis and cancer chemotherapy, Cancer Res. 48, 2946–2954.

Oeda, K. Sakaki, T. & Ohkawa, H. (1985) Expression of rat liver cytochrome P-450MC cDNA in Saccharomyces cerevisiae, DNA 4, 203–210.

Pompon, D. (1988) cDNA cloning and functional expression in yeast *Saccharomyces cerevisiae* of b-naphthoflavone-induced rabbit liver cytochromes P-450 LM4 and LM6, *Eur. J. Biochem.* 177, 285–293.

Stotz, A. & Linder, P. (1990) The ADE2 gene from *Saccharomyces cerevisiae*: sequence and new vectors, *Gene* (Amst.) 95, 91–98.

Truan, G. Cullin, C. Reisdorf, P. Urban, P. & Pompon, D. (1993) Enhanced in vivo monooxygenase activities of mammalian cytochrome P450s in engineered yeast cells producing high levels of NADPH-cytochrome P450 reductase and human cytochrome b5, *Gene* (Amst) 125, 49–55.

Truan, G. Epinat, J. C. Rougeulle, C. Cullin, C. & Pompon, D. (1994) Cloning and characterization of yeast cytochrome b5-encoding gene which suppresses ketoconazole hypersensitivity in an NADPH-P-450 reductase-deficient strain, *Gene* (Amst.) 149, 123–127.

Urban, P. Cullin, C. & Pompon, D. (1990) Maximizing the expression of mammalian cytochrome P-450 monooxygenase activities in yeast cells, Biochimie (Paris) 72, 463–472.

Urban, P. Traun, G. Gautier, J. C. & Pompon D. (1993) Xenobiotic metabolism in humanized yeast: engineered yeast cells producing human NADPH-cytochrome P450 reductase, cytochrome b5, epoxide hydrolase and cytochrome P450s, *Biochem Soc Transact* 21, 1028–1033.

Zuber, M. X. Simpson, E. R. & Waterman, M. R. (1986) Expression of bovine 17a-hydroxylase cytochrome P-450s cDNA in nonsteroidogenic (COSI) cells, *Science* 234, 1258–1261.

Patent No. WO 93/02200: Souches de levure avec intégration stable de genes heterologues (Yeast strains in which heterologous genes are stably integrated).

Patent No. WO 94/01564: Souche de levure permettant la co-expression d'une activité mono-oxygénase de cytochrome P450 de plante et d'une NADPH-cytochrome P450-réductaseendogène ou hétérologue et son utilisation à des fins de bioconversion (Yeast' strain which is able to coexpress a plant cytochrome P450 monooxygenase activity and an endogenous or heterologous NADPH-cytochrome P450 reductase, and its use for bioconversion purposes).

What is claimed is:

1. An in vitro method for determining the metabolites of a chemical compound, the method comprising:
    (a) providing a genetically-modified yeast cell comprising a nucleic acid encoding human NADPH-cytochrome P450 reductase and a nucleic acid encoding human cytochrome b5, wherein the genes encoding endogenous yeast NADPH-cytochrome P450 reductase and endogenous yeast cytochrome b5 have been inactivated;
    (b) contacting the chemical compound with an enzyme preparation isolated from the yeast cell; and
    (c) determining the metabolites arising from the degradation of the chemical compound.

2. The method of claim 1, wherein the nucleic acid encoding human NADPH-cytochrome P450 reductase and the nucleic acid encoding human cytochrome b5 are cDNAs.

3. The method of claim 1, wherein the nucleic acid encoding human NADPH-cytochrome P450 reductase is integrated into the genome of the yeast cell.

4. The method of claim 1, wherein the nucleic acid encoding human cytochrome b5 is integrated into the genome of the yeast cell.

5. The method of claim 1, wherein the yeast cell further comprises at least one nucleic acid encoding human cytochrome P450.

6. The method of claim 1, wherein the yeast cell is haploid.

7. The method of claim 1, wherein the yeast cell is *Saccharomyces cerevisiae*.

8. The method of claim 1, wherein the nucleic acid encoding human NADPH-cytochrome P450 reductase is under control of a yeast glyceraldehyde phosphodehydrogenase (GAPDH) promoter.

9. The method of claim 1, wherein the nucleic acid encoding human cytochrome b5 is under control of a yeast phosphoglycerate kinase (PGK) promoter and the nucleic acid encoding human NADPH-cytochrome P450 reductase is under control of a yeast glyceraldehyde phosphodehydrogenase (GAPDH)promoter.

10. The method of claim 1, wherein the nucleic acid encoding human cytochrome b5 is under control of a yeast phosphoglycerate kinase (PGK) promoter.

11. The method of claim 1, wherein the nucleic acid encoding human NADPH-cytochrome P450 reductase and the nucleic acid encoding human cytochrome b5 are part of a plasmid in the yeast cell.

12. The method of claim 1, wherein the nucleic acid encoding human NADPH-cytochrome P450 reductase is in a plasmid.

13. The method of claim 1, wherein the nucleic acid encoding human cytochrome b5 is in a plasmid.

14. The method of claim 2, wherein at least one of the nucleic acids is under control of a constitutive promoter or inducible promoter.

15. The method of claim 5, wherein the nucleic acid encoding human cytochrome P450 is in a plasmid.

16. The method of claim 11, wherein:
    (i) the nucleic acid encoding human NADPH-cytochrome P450 reductase is under control of a GAL10-CYC1 promoter; and
    (ii) the nucleic acid encoding human cytochrome b5 is under control of a GAL10-CYC1 promoter, a phosphoglycerate (PGK) promoter, or a glyceraldehyde phosphodehydrogenase (GAPDH) promoter, wherein when the nucleic acid encoding human NADPH-cytochrome P450 reductase and the nucleic acid encoding human cytochrome b5 are each under control of GAL10-CYC1 promoters, then the GAL10-CYC1 promoters are present in opposite orientations in the plasmid.

17. The method of claim 14, wherein the constitutive promoter is a promoter of a glyceraldehyde phosphodehydrogenase gene, a promoter of a phosphoglycerate kinase gene, or an endogenous promoter of a yeast cytochrome b5 gene.

18. The method of claim 14, wherein the inducible promoter is a GAL10 promoter or a GAL10-CYC1 promoter.

19. The method of claim 15, wherein the yeast cell further comprises an additional copy of the nucleic acid encoding human cytochrome b5 on said plasmid or integrated into the yeast cell genome.

20. An in vitro method for determining the metabolites of a chemical compound, the method comprising:
(a) providing a genetically-modified yeast cell comprising a nucleic acid encoding human NADPH-cytochrome P450 reductase and a nucleic acid encoding human cytochrome b5, wherein the genes encoding endogenous yeast NADPH-cytochrome P450 reductase and endogenous yeast cytochrome b5 have been inactivated;
(b) contacting the chemical compound to the yeast cell; and
(c) determining the metabolites arising from the degradation of the chemical compound.

21. The method of claim 20, wherein the nucleic acid encoding human NADPH-cytochrome P450 reductase and the nucleic acid encoding human cytochrome b5 are cDNAs.

22. The method of claim 20, wherein the nucleic acid encoding human NADPH-cytochrome P450 reductase is integrated into the genome of the yeast cell.

23. The method of claim 20, wherein the nucleic acid encoding human cytochrome b5 is integrated into the genome of the yeast cell.

24. The method of claim 20, wherein the yeast cell further comprises at least one nucleic acid encoding human cytochrome P450.

25. The method of claim 20, wherein the yeast cell is haploid.

26. The method of claim 20, wherein the yeast cell is *Saccharomyces cerevisiae*.

27. The method of claim 20, wherein the nucleic acid encoding human NADPH-cytochrome P450 reductase is under control of a yeast glyceraldehyde phosphodehydrogenase (GAPDH) promoter.

28. The method of claim 20, wherein the nucleic acid encoding human cytochrome b5 is under control of a yeast phosphoglycerate kinase (PGK) promoter and the nucleic acid encoding human NADPH-cytochrome P450 reductase is under control of a yeast glyceraldehyde phosphodehydrogenase (GAPDH) promoter.

29. The method of claim 20, wherein the nucleic acid encoding human cytochrome b5 is under control of a yeast phosphoglycerate kinase (PGK) promoter.

30. The method of claim 20, wherein the nucleic acid encoding human NADPH-cytochrome P450 reductase and the nucleic acid encoding human cytochrome b5 are part of a plasmid in the yeast cell.

31. The method of claim 20, wherein the nucleic acid encoding human NADPH-cytochrome P450 reductase is in a plasmid.

32. The method of claim 20, wherein the nucleic acid encoding human cytochrome b5 is in a plasmid.

33. The method of claim 21, wherein at least one of the nucleic acids is under control of a constitutive promoter or inducible promoter.

34. The method of claim 24, wherein the nucleic acid encoding human cytochrome P450 is in a plasmid.

35. The method of claim 30, wherein:
(i) the nucleic acid encoding human NADPH-cytochrome P450 reductase is under control of a GAL10-CYC1 promoter; and
(ii) the nucleic acid encoding human cytochrome b5 is under control of a GAL10-CYC1 promoter, a phosphoglycerate (PGK) promoter, or a glyceraldehyde phosphodehydrogenase (GAPDH) promoter, wherein when the nucleic acid encoding human NADPH-cytochrome P450 reductase and the nucleic acid encoding human cytochrome b5 are each under control of GAL10-CYC1 promoters, then the GAL10-CYC1 promoters are present in opposite orientations in the plasmid.

36. The method of claim 33, wherein the constitutive promoter is a promoter of a glyceraldehyde phosphodehydrogenase gene, a promoter of a phosphoglycerate kinase gene, or an endogenous promoter of a yeast cytochrome b5 gene.

37. The method of claim 33, wherein the inducible promoter is a GAL10 promoter or a GAL10-CYC1 promoter.

38. The method of claim 34, wherein the yeast cell further comprises an additional copy of the nucleic acid encoding human cytochrome b5 on said plasmid or integrated into the yeast cell genome.

39. A process for producing a metabolite, the process comprising contacting a compound degraded by a cytochrome P450 enzyme system into a metabolite with a genetically modified yeast strain comprising a nucleic acid encoding human NADPH-cytochrome P450 reductase and a nucleic acid encoding human cytochrome b5, wherein the human NADPH-cytochrome reductase and the human cytochrome b5 are part of the cytochrome P450 enzyme system, and wherein the genes encoding the endogenous yeast cytochrome b5 and cytochrome P450 reductase have been inactivated.

40. A process for producing a metabolite, the process comprising contacting a compound degraded by a cytochrome P450 enzyme system into a metabolite with an enzyme preparation isolated from a genetically modified yeast strain comprising a cytochrome P450 enzyme system further comprising a nucleic acid encoding human NADPH-cytochrome P450 reductase and a nucleic acid encoding human cytochrome b5, wherein the human NADPH-cytochrome P450 reductase and the human cytochrome b5 are part of the cytochrome P450 enzyme system, and wherein the genes encoding the endogenous yeast cytochrome b5 and cytochrome P450 reductase have been inactivated.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GCGGATCCAT GGGAGACAGT CACGTGG     27

(2) INFORMATION FOR SEQ ID NO: 2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

CGGAATTCAG ATCTAGCTCC ACACGTCCAG G     31

(2) INFORMATION FOR SEQ ID NO: 3:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

CCAAGCTTGA GTTTATCATT ATCAATACTC G     31

(2) INFORMATION FOR SEQ ID NO: 4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CGGATCCTAT TTATGTGTGT TTATTCGAAA CTAAGTTCTT GG                          42
```

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GGATCCGAGC GGGTAATAGC CTGGAGTTTC C                                     31
```

(2) INFORMATION FOR SEQ ID NO: 6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
CCGACTGCTC TGCCATGATT GTTTGATATT TTATGTTGTA GTTGATTG                   48
```

(2) INFORMATION FOR SEQ ID NO: 7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
CCTATACATG GCAGAGGACT GAATTCTTTT TCTTCCAGAA TAGCCCACAC                 50
```

(2) INFORMATION FOR SEQ ID NO: 8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
GGAGATCTGT GACATACTTC TATGCGATAT AG                                    32
```

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TTGAAGGTTC AACATCAATT GATTG                                             25

(2) INFORMATION FOR SEQ ID NO: 10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GTGTGGCGGC CGCCTCCTTG TCAATATTAA TGTTAAAG                                38

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CAAGGAGGCG GCCGCCACAC AAAAAGTTAG GTGT                                   34

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TCTGCTTCCC TAGAACCTTC TTATG                                             25

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

CAGATCTGCA TGCCTAAAGT TTACAGTTAC C                                      31

(2) INFORMATION FOR SEQ ID NO: 14:

(i) SEQUENCE CHARACTERISTICS:
        (A) LENGTH: 42 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 14:

CGGATTCTGC AGTTATTCGT TCAACAAATA ATAAGCAACA CC                42

(2) INFORMATION FOR SEQ ID NO: 15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CCGAATTCTG ATCAGTCCTC TGCCATGTAT AGG                         33

(2) INFORMATION FOR SEQ ID NO: 16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GCCCAGATCT ATGGCAGAGC AGTCGGACG                              29

(2) INFORMATION FOR SEQ ID NO: 17:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GGCGTTACCC AACTTAATCG CCTTGCACAT CCCCCTTTCG CCGGAACGTG CTGCTACTCA    60

TCCTAGTCC                                                    69

(2) INFORMATION FOR SEQ ID NO: 18:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GGGAAGGGCG ATCGGTGCGG GCCTCTTCGC TATTACGCCA GCTGGCCGAT TCATTAATGC    60

AGCTGGGCGG                                                   70

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single

```
            (D) TOPOLOGY: linear (ii) MOLECULE TYPE: cDNA (xi) SEQUENCE DESCRIPTION: SEQ ID NO: 19:

CCCCCCTTTC GCCAGGGAAC GTGC                                              24

(2) INFORMATION FOR SEQ ID NO: 20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 20:

CGGTAGGTAT TGATTGTAAT TCTG                                              24

(2) INFORMATION FOR SEQ ID NO: 21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 21:

GGCATGCATG TGCTCTGTAT G                                                 21
```